US010674937B2

(12) United States Patent  
Colvin, Jr. et al.

(10) Patent No.: US 10,674,937 B2  
(45) Date of Patent: *Jun. 9, 2020

(54) INTEGRATED CATALYTIC PROTECTION OF OXIDATION SENSITIVE MATERIALS

(71) Applicant: Senseonics, Incorporated, Germantown, MD (US)

(72) Inventors: Arthur E. Colvin, Jr., Mt. Airy, MD (US); Hui Jiang, Clarksburg, MD (US)

(73) Assignee: Senseonics, Incorporated, Germantown, MD (US)

( * ) Notice: Subject to any disclaimer, the term of this patent is extended or adjusted under 35 U.S.C. 154(b) by 90 days.

This patent is subject to a terminal disclaimer.

(21) Appl. No.: 15/623,474

(22) Filed: Jun. 15, 2017

(65) Prior Publication Data

US 2018/0146885 A1    May 31, 2018

Related U.S. Application Data

(63) Continuation of application No. 13/421,013, filed on Mar. 15, 2012, now Pat. No. 9,681,824.

(Continued)

(51) Int. Cl.
*A61B 5/1455* (2006.01)
*A61B 5/07* (2006.01)
(Continued)

(52) U.S. Cl.
CPC .............. *A61B 5/076* (2013.01); *A61B 5/145* (2013.01); *A61B 5/1459* (2013.01);
(Continued)

(58) Field of Classification Search
None
See application file for complete search history.

(56) References Cited

U.S. PATENT DOCUMENTS

| 5,517,313 A | 5/1996 | Colvin, Jr. |
| 5,772,864 A | 6/1998 | Moller et al. |

(Continued)

FOREIGN PATENT DOCUMENTS

| JP | S63-291595 A | 11/1988 |
| JP | 2001-513350 A | 9/2001 |

(Continued)

OTHER PUBLICATIONS

PCT International Search Report, issued in PCT/US2012/029209 dated Jun. 8, 2012, 17 pages.

(Continued)

*Primary Examiner* — Eric F Winakur  
*Assistant Examiner* — Marjan Fardanesh  
(74) *Attorney, Agent, or Firm* — Rothwell, Figg, Ernst & Manbeck, P.C.

(57) ABSTRACT

An implantable device with in vivo functionality, where the functionality of the device is negatively affected by ROS typically associated with inflammation reaction as well as chronic foreign body response as a result of tissue injury, is at least partially surrounded by a protective material, structure, and/or a coating that prevents damage to the device from any inflammation reactions. The protective material, structure, and/or coating is a biocompatible metal, preferably silver, platinum, palladium, gold, manganese, or alloys or oxides thereof that decomposes reactive oxygen species (ROS), such as hydrogen peroxide, and prevents ROS from oxidizing molecules on the surface of or within the device. The protective material, structure, and/or coating thereby prevents ROS from degrading the in vivo functionality of the implantable device.

26 Claims, 25 Drawing Sheets

Related U.S. Application Data

(60) Provisional application No. 61/527,368, filed on Aug. 25, 2011, provisional application No. 61/452,893, filed on Mar. 15, 2011.

(51) Int. Cl.
  *A61B 5/145* (2006.01)
  *A61B 5/1459* (2006.01)
(52) U.S. Cl.
  CPC .... *A61B 5/14532* (2013.01); *A61B 2562/028* (2013.01); *A61B 2562/162* (2013.01); *A61B 2562/18* (2013.01)

(56) References Cited

U.S. PATENT DOCUMENTS

| | | | |
|---|---|---|---|
| 5,833,603 A | 11/1998 | Kovacs et al. | |
| 5,894,351 A | 4/1999 | Colvin, Jr. | |
| 5,910,661 A | 6/1999 | Colvin, Jr. | |
| 5,917,605 A | 6/1999 | Colvin, Jr. | |
| 5,922,183 A | 7/1999 | Rauh | |
| 6,189,536 B1 | 2/2001 | Martinez et al. | |
| 6,304,766 B1 | 10/2001 | Colvin, Jr. | |
| 6,330,464 B1 | 12/2001 | Colvin, Jr. et al. | |
| 6,344,360 B1 | 2/2002 | Colvin et al. | |
| 6,400,974 B1 | 6/2002 | Lesho | |
| 6,584,335 B1 | 6/2003 | Haar et al. | |
| 6,709,379 B1 | 3/2004 | Brandau et al. | |
| 6,794,195 B2 | 9/2004 | Colvin, Jr. | |
| 6,800,451 B2 | 10/2004 | Daniloff et al. | |
| 6,940,590 B2 | 9/2005 | Colvin, Jr. et al. | |
| 7,135,342 B2 | 11/2006 | Colvin, Jr. et al. | |
| 7,157,723 B2 | 1/2007 | Colvin et al. | |
| 7,190,445 B2 | 3/2007 | Colvin, Jr. et al. | |
| 7,308,292 B2 | 12/2007 | Colvin et al. | |
| 7,375,347 B2 | 5/2008 | Colvin, Jr. et al. | |
| 7,553,280 B2 | 6/2009 | Lesho | |
| 7,713,745 B2 | 5/2010 | Colvin, Jr. et al. | |
| 7,783,333 B2 | 8/2010 | Brister et al. | |
| 7,800,078 B2 | 9/2010 | Colvin, Jr. et al. | |
| 7,851,225 B2 | 12/2010 | Colvin, Jr. et al. | |
| 7,939,832 B2 | 5/2011 | Colvin et al. | |
| 8,073,548 B2 | 12/2011 | Colvin, Jr. et al. | |
| 8,143,068 B2 | 3/2012 | Colvin, Jr. et al. | |
| 8,233,953 B2 | 7/2012 | Colvin, Jr. | |
| 8,415,184 B2 | 4/2013 | Colvin et al. | |
| 8,657,745 B2 | 2/2014 | Brauker et al. | |
| 8,923,947 B2 | 12/2014 | Shults et al. | |
| 8,940,544 B2 | 1/2015 | Suri et al. | |
| 9,339,222 B2 | 5/2016 | Simpson et al. | |
| 9,797,909 B2 | 10/2017 | Paterson et al. | |
| 9,931,067 B2 | 4/2018 | Shults et al. | |
| 9,970,940 B2 | 5/2018 | Crane et al. | |
| 10,117,613 B2 | 11/2018 | Wisniewski et al. | |
| 2004/0063167 A1 | 4/2004 | Kaastrup et al. | |
| 2005/0074602 A1 | 4/2005 | Bjursten et al. | |
| 2005/0095174 A1 | 5/2005 | Wolf | |
| 2005/0096587 A1 | 5/2005 | Santini, Jr. et al. | |
| 2005/0215871 A1 | 9/2005 | Feldman et al. | |
| 2005/0221277 A1 | 10/2005 | Kawanishi | |
| 2005/0227242 A1 | 10/2005 | Colvin, Jr. et al. | |
| 2005/0234316 A1 | 10/2005 | Colvin, Jr. et al. | |
| 2006/0129050 A1 | 6/2006 | Martinson et al. | |
| 2006/0270922 A1 | 11/2006 | Brauker et al. | |
| 2006/0282042 A1 | 12/2006 | Walters et al. | |
| 2007/0014726 A1 | 1/2007 | Merical et al. | |
| 2007/0027384 A1 | 2/2007 | Brister et al. | |
| 2007/0114138 A1 | 5/2007 | Krasteva et al. | |
| 2007/0191701 A1 | 8/2007 | Feldman et al. | |
| 2008/0125838 A1 | 5/2008 | Francis | |
| 2008/0228051 A1 | 9/2008 | Shults et al. | |
| 2009/0264718 A1 | 10/2009 | Lesho | |
| 2010/0024526 A1 | 2/2010 | Colvin, Jr. et al. | |
| 2010/0202966 A1 | 8/2010 | Gross et al. | |
| 2010/0298674 A1 | 11/2010 | Colvin, Jr. et al. | |
| 2011/0236989 A1 | 9/2011 | Suri et al. | |
| 2011/0255255 A1 | 10/2011 | Colvin et al. | |
| 2011/0295128 A1* | 12/2011 | Yuasa | A61B 5/021 600/485 |
| 2012/0053427 A1 | 3/2012 | Markle et al. | |
| 2012/0238842 A1 | 9/2012 | Colvin, Jr. et al. | |

FOREIGN PATENT DOCUMENTS

| | | |
|---|---|---|
| JP | 2002-523774 A | 7/2002 |
| JP | 2005-315871 A | 11/2005 |
| JP | 2007-532901 A | 11/2007 |
| JP | 2008-506469 A | 3/2008 |
| KR | 2003-0055609 A | 7/2003 |
| TW | 200838985 A | 10/2008 |
| TW | 201041612 A | 12/2010 |
| WO | 03/063925 A1 | 8/2003 |
| WO | 2005/051170 A2 | 6/2005 |
| WO | 2005/078424 A1 | 8/2005 |
| WO | 2007/067743 A2 | 6/2007 |
| WO | 2008/141241 A1 | 11/2008 |
| WO | 2010/118335 A1 | 10/2010 |
| WO | 2010/123972 A1 | 10/2010 |
| WO | 2011/097586 A1 | 8/2011 |
| WO | 2011/101626 A1 | 8/2011 |

OTHER PUBLICATIONS

Brian Woodward et al., "The Sustainable Importance of Platinum in Biomedical Applications," MDDI Medical Device and Diagnostic Industry News Products and Suppliers (http://www.mddionline.com/print/7951), May 20, 2011, 9 pages.

\* cited by examiner

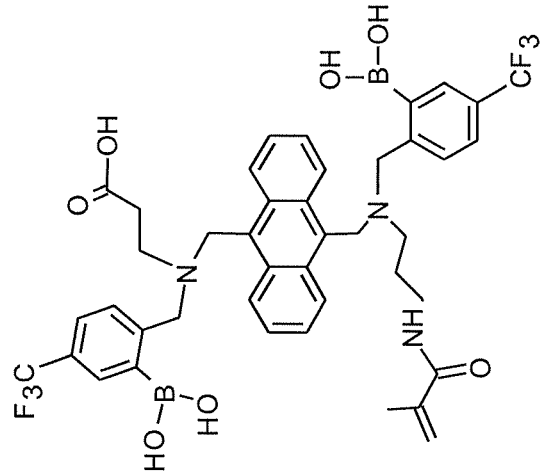
5-Trifluoromethyl (27b)
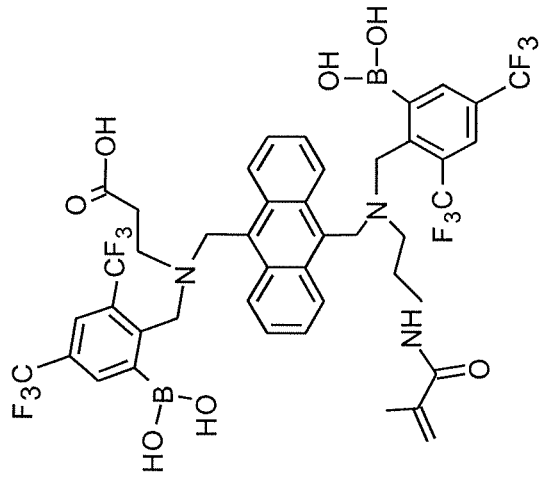
3, 5-bis(trifluoromethyl) (27a)
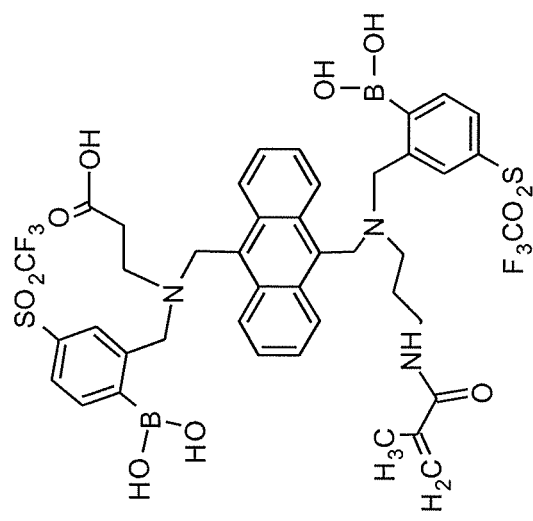
4-Trifluoromethylsulfone (21)
FIG. 2B-2

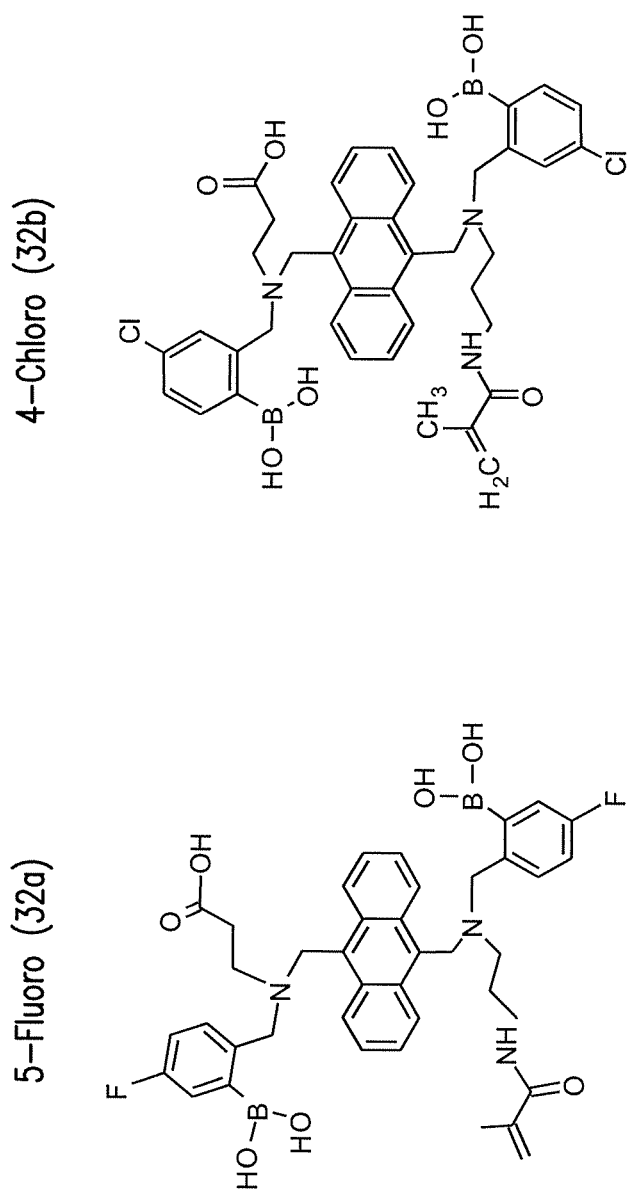

Saddle cut graft encasement

Full cut graft encasement

Sputtered saddle cut graft concept

Saddle cut graft encasement

Oxidation: 0.6mL 0.2mM $H_2O_2$/0.14M NaCl/10mM phosphate, pH7.4, 37°C, 24h.

Oxidation: 0.6mL 0.2mM $H_2O_2$/0.14M NaCl/10mM phosphate, pH7.4, 37°C, 24h.

INTEGRATED CATALYTIC PROTECTION OF OXIDATION SENSITIVE MATERIALS

This application is a continuation of and claims priority to pending U.S. patent application Ser. No. 13/421,013, filed Mar. 15, 2012, which claims the benefit of prior-filed provisional patent application U.S. 61/452,893 which was filed on Mar. 15, 2011, and also claims the benefit of prior-filed provisional patent application U.S. 61/527,368 which was filed on Aug. 25, 2011, the contents of both of which are hereby incorporated by reference in their entireties. This invention was not made with government support under any government contract awarded by any Federal agency, and thus the government does not retain rights in the invention.

BACKGROUND OF THE INVENTION

Field of the Invention

The present invention relates to the catalytic protection of materials and devices that are sensitive to oxidation by integrating the catalytic protection with the material or device. The present invention particularly relates to devices designed to be implanted or inserted into the body of an animal, including humans. More particularly, the invention relates to (but is not limited to) electro-optical-based sensing devices for detecting the presence or concentration of an analyte in a medium which are characterized by being totally self-contained and of an extraordinarily compact size which permits the device to be implanted in humans for in situ detection of various analytes.

Description of Related Art

None of the references described or referred to herein are admitted to be prior art to the claimed invention.

Implantable devices for monitoring various physiological conditions are known. They include, for example, the sensors described in U.S. Pat. No. 5,517,313 to Colvin; U.S. Pat. No. 5,910,661 to Colvin; U.S. Pat. No. 5,917,605 to Colvin; U.S. Pat. No. 5,894,351 to Colvin; U.S. Pat. No. 6,304,766 to Colvin; U.S. Pat. No. 6,344,360 to Colvin et al.; U.S. Pat. No. 6,330,464 to Colvin; U.S. Pat. No. 6,400,974 to Lesho; U.S. Pat. No. 6,794,195 to Colvin; U.S. Pat. No. 7,135,342 to Colvin et al.; U.S. Pat. No. 6,940,590 to Colvin et al.; U.S. Pat. No. 6,800,451 to Daniloff et al.; U.S. Pat. No. 7,375,347 to Colvin et al.; U.S. Pat. No. 7,157,723 to Colvin et al.; U.S. Pat. No. 7,308,292 to Colvin et al.; U.S. Pat. No. 7,190,445 to Colvin et al., U.S. Pat. No. 7,553,280 to Lesho; U.S. Pat. No. 7,800,078 to Colvin, Jr. et al.; U.S. Pat. No. 7,713,745 to Colvin, Jr. et al.; U.S. Pat. No. 7,851,225 to Colvin, Jr. et al.; U.S. Pat. No. 7,939,832 to J. Colvin et al.; and in the following U.S. patent applications: Ser. No. 10/825,648 to Colvin et al. filed Apr. 16, 2004; Ser. No. 10/923,698 to Colvin et al. filed Aug. 24, 2004; Ser. No. 11/447,980 to Waters et al. filed Jun. 7, 2006; Ser. No. 11/487,435 to Merical et al. filed Jul. 17, 2006; Ser. No. 11/925,272 to Colvin filed Oct. 26, 2007; Ser. No. 12/508,727 to Colvin, Jr. et al. filed Jul. 24, 2009; Ser. No. 12/493,478 to Lesho filed Jun. 29, 2009; Ser. No. 12/764,389 to Colvin, Jr. et al. filed Apr. 21, 2010; Ser. No. 12/966,693 to Colvin, Jr. et al. filed Dec. 13, 2010; Ser. No. 13/103,561 to Colvin et al. filed May 9, 2011; and Ser. No. 13/171,711 to J. Colvin et al. filed Jun. 29, 2011; the contents of all of the foregoing are incorporated by reference herein. Where terms used in the current application are in conflict with use of the terms in the incorporated references, the definitions in the current application will be controlling.

When a foreign object enters a body, there is an immediate immunological response (i.e., inflammation) to eliminate or neutralize that foreign object. When the foreign object is an intentionally implanted material, device, or sensor, the inflammation response can cause damage to or otherwise negatively impact the functionality of the implant. Thus, a need exists for an implantable device (or material) that can endure the biochemical activity of an inflammation response and chronic foreign body response, i.e. oxidation, such that the efficacy and useful life of the device is not adversely impacted. A corresponding need exists for a method of manufacturing or treating an implantable device (or material) such that it can endure the biochemical activity of inflammation and foreign body response without significant loss of efficacy or useful life.

The problem of in vivo oxidation and the corresponding in vivo destruction of materials and function by reactive oxygen species (ROS) associated with inflammation response is well known. As used herein, ROS stands for reactive oxygen species, highly reactive oxygen species, or reactive oxygen radical species, and includes peroxides such as hydrogen peroxide. Some means of at least partially protecting an implanted device or material from destructive oxidation have included the use of antioxidants that may be either immobilized within or leached from an implanted device or material into the in vivo surrounding space. Systemic drugs such as anti-inflammatory varieties, superoxide dismutase mimetics, and other similar agents may also be leached or injected locally into the region around the implanted device or material in combination with, or alternatively to, antioxidants. In such cases, the device or material must either include or leach a drug or substance into the local in vivo environment and thus can become influential on wound healing, and causes the device itself to become a drug delivery mechanism in addition to its original intended purpose. Adding in the additional drug/substance release features may add complexity, variability, and uncertainty into an implant design and may complicate proving the safety and efficacy of the device or material. Also, since the inflammation response is a normal part of healing that serves to kill any bacteria that may be in the wound, drugs or leached reagents which may disable this otherwise normal aspect of wound healing might compromise the patient. Ideally, an integrated device solution which can protect just the susceptible and vulnerable component(s) of the implant would be the safest and most efficient means of solving the problem.

SUMMARY OF THE INVENTION

Aspects of the invention are embodied, but not limited to, the various forms of the invention described below.

In one aspect, the present invention relates to a device comprising an implantable device which has an in vivo functionality, as well as a protective material in close proximity to the surface of the implantable device. The protective material prevents or reduces degradation or interference of the implantable device due to inflammation reactions and/or foreign body response. Further, the protective material can comprise a metal or metal oxide which catalytically decomposes or inactivates in vivo reactive oxygen species or biological oxidizers.

In another aspect, the present invention relates to a device comprising an implantable device which has an in vivo functionality as well as a protective coating deposited on the surface of the implantable device. The protective coating prevents or reduces degradation or interference of the implantable device due to inflammation reactions and/or foreign body response. Further, the protective coating can comprise a metal or metal oxide which catalytically decomposes or inactivates in vivo reactive oxygen species or biological oxidizers.

In another aspect, the present invention relates to a method for using an implantable device in in vivo applications. The method comprises at least providing an implantable device which has an in vivo functionality. The implantable device has a layer of a protective coating applied onto the device, wherein the protective coating applied by the method prevents or reduces degradation or interference of the implantable device due to inflammation reactions and/or foreign body response. The protective coating applied by the method can comprise a metal or metal oxide which catalytically decomposes or inactivates in vivo reactive oxygen species or biological oxidizers. The method further comprises implanting the implantable device in a subject body.

In another aspect, the present invention relates to a method for detecting the presence or concentration of an analyte in an in vivo sample. The method comprises at least exposing the in vivo sample to a device having a detectable quality that changes when the device is exposed to an analyte of interest. The device comprises in part a layer of a protective coating, wherein the protective coating prevents or reduces degradation or interference of the device from inflammation reactions and/or foreign body response. The protective coating can comprise a metal or metal oxide which catalytically decomposes or inactivates in vivo reactive oxygen species or biological oxidizers, such that the device has enhanced resistance to degradation or interference by oxidation as compared to a corresponding device without the protective coating. The method further comprises measuring any change in the detectable quality to thereby determine the presence or concentration of an analyte of interest in the in vivo sample.

In another aspect, the present invention is an implantable glucose sensor for determining the presence or concentration of glucose in an animal. The sensor can comprise a sensor body having an outer surface surrounding the sensor body, a radiation source in said sensor body which emits radiation within said sensor body, an indicator element that is affected by the presence or concentration of glucose in said animal, where the indicator element is positioned in close proximity to at least a portion of the outer surface of the sensor body. Further, the sensor can comprise a photosensitive element located in the sensor body, positioned to receive radiation within the sensor body, where the photosensitive element is configured to emit a signal responsive to radiation received from an indicator element and which is indicative of the presence or concentration of glucose in an animal. Moreover, the sensor can comprise a protective barrier comprising silver, palladium, platinum, manganese, or alloys, or gold-inclusive alloys, or combinations thereof, at least partially surrounding said indicator element.

In another aspect, the present invention can be a pacemaker comprising an electrical generator, lead wires connected to said electrical generator, and a protective material in close proximity to or comprising at least a surface of the pacemaker. The protective material can prevent or reduce degradation or interference of the pacemaker due to inflammation reactions and/or foreign body response. Further, the protective material can comprise a metal or metal oxide which catalytically decomposes or inactivates in vivo reactive oxygen species or biological oxidizers.

These and other features, aspects, and advantages of the present invention will become apparent to those skilled in the art after considering the following detailed description, appended claims and accompanying drawings.

DETAILED DESCRIPTION OF THE PREFERRED EMBODIMENTS

Figure 1A:
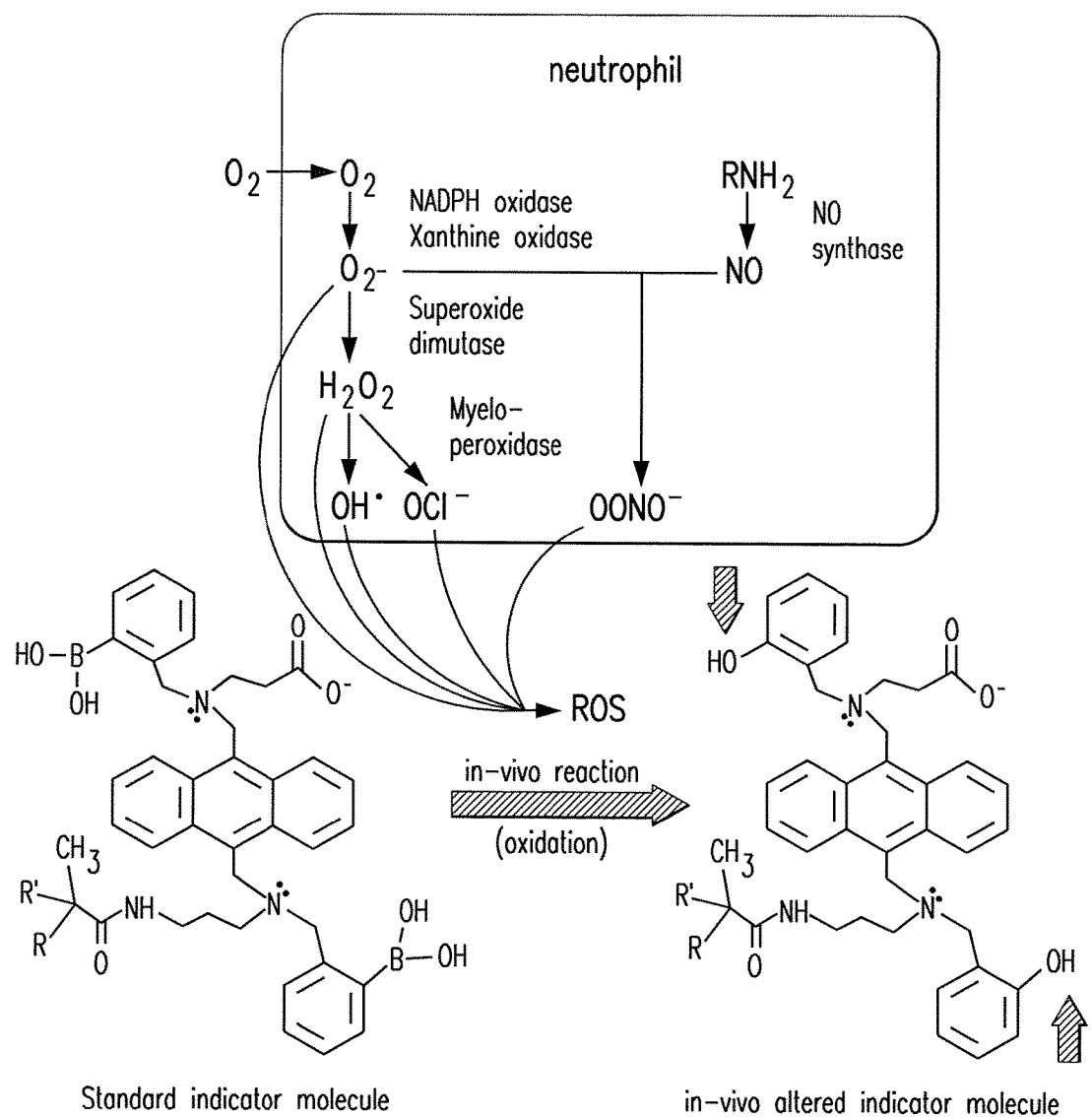
FIG. 1A is an illustration of the chemical reaction where an unprotected —B(OH)$_2$ recognition element of a glucose indicator is oxidized when exposed to in vivo reactive oxygen species (ROS).

The present invention is embodied in an apparatus and/or material, and methods of using such an apparatus and/or material, designed to be implanted into a living body and to perform an in vivo functionality. Such a system may preferably comprise an implantable sensor, and more preferably, an implantable glucose monitoring sensor. Such a sensor may have a smooth and rounded, oblong, oval, or elliptical shape (e.g., a bean- or pharmaceutical capsule-shape). While the preferred embodiment of the device described herein is that of a glucose detection sensor, the present invention is not limited to only implantable glucose sensors, or only implantable sensors, or even limited to only sensors.

An object of the invention is to protect an implantable sensor, material, or device which may be either destroyed, weakened (in either signal or mechanical strength), or suffer diminished function or utility as a result of oxidation from ROS typically due to inflammation reaction. Such diminished function or utility may be manifested as the loss of mechanical strength, pitting, leaching undesirable degradation products into the body, tissue damage from surface deformation, or the loss of kinetic profile of a drug delivery system. The inflammation is often stimulated by the implantation procedure, the implanted device, or both. A further object of the invention is to incorporate a feature included within the design of a sensor or other implantable device or component (which device or component may be susceptible to damage by ambient reactive oxygen species) that will protect the implanted sensor or device from oxidative damage or degradation. Highly reactive oxygen species (ROS) known to occur within living systems and cause damage include, for example, hydrogen peroxide ($H_2O_2$), hydroxyl radical ($OH^-$), hypochlorite ($OCl^-$), peroxynitrite ($OONO^-$), and superoxide ($O_2^-$). Of these ROS species, hydrogen peroxide appears to be the most problematic in causing damage to an implanted sensor or device in vivo. Thus, a specific object of the invention is to protect the in vivo function of a sensor or device from signal loss and shortened useful life due to hydrogen peroxide and other ROS produced within the body.

Certain metals such as silver, palladium, and platinum, and oxides of those and other metals, such as manganese, have a catalytic functionality that decomposes hydrogen peroxide into molecular oxygen and water. Thus, embodiments of the present invention seek to use such metals in conjunction with materials sensitive to oxidation to prevent hydrogen peroxide from oxidizing the materials susceptible to oxidation. In particular, the material sensitive to oxidation may be indicator macromolecules dispersed throughout a porous sensor graft according to embodiments of the invention. As used herein, "indicator macromolecule" refers to a structure comprising an indicator monomer co-polymerized with a relatively hydrophilic molecule or structure. In some embodiments of the invention, the metals or metal oxides that catalyze the decomposition of hydrogen peroxide are combined with materials sensitive to oxidation by various configurations in close proximity to the sensitive materials, such as in the form of a wire, mesh, or coil at least partially surrounding the material to be protected. In further embodiments of the invention, the metals that have a catalytic functionality may be alloys with other metals, such as gold, to take advantage of the properties of such other metals. In other embodiments of the invention, the metals that catalyze the decomposition of hydrogen peroxide are combined with materials sensitive to oxidation by coating areas in close proximity to the sensitive materials with metal or metal oxides via sputter deposition. In embodiments, a portion of the material sensitive to oxidation may be coated with catalyst to provide protection to the remaining adjacent portion. In embodiments, catalytic porous or ROS diffusive contacting layers can be positioned between the ROS and the species to be protected. Embodiments of the invention may act as catalytic selective barriers or permselective diffusion barriers.

Hydrogen peroxide is considered the most problematic of the ROS that destroys implant functionality. The other four ROS species do not appear to have a significant effect on implant functionality as these species are either destroyed, not stimulated to production, or converted into peroxide in vivo. The more reactive superoxide is converted to hydrogen peroxide naturally by superoxide dismutase. Hydroxyl radicals are so extremely reactive that they cannot diffuse very far before reacting with something and are, therefore, limited in some embodiments to a distance on the scale of angstroms on the surface of an implanted device or material. Hypochlorite, in the presence of hydrogen peroxide, is decomposed into water, oxygen, and a chloride ion. Nitric oxide (NO) radical, in the presence of superoxide in vivo, produces peroxynitrite which is decomposed via ambient carbon dioxide which itself acts as a decomposition catalyst. Hydrogen peroxide is both reactive and sufficiently stable to have the persistence to diffuse throughout a porous sensor graft and indicator region of a sensor and oxidize all indicator molecules present, resulting in a loss of sensor function in vivo.

Devices useful in the practice of the present invention include those described in the patents and publications listed above and incorporated by reference herein. In a preferred embodiment, the device is an implantable glucose monitoring sensor such as the sensors described in U.S. Pat. Nos. 7,553,280, 7,800,078, or 7,713,745. In some embodiments of the present invention, the sensor may include a sensor body, a porous graft coated over, imbedded within a pocket, or immobilized onto the exterior surface of the sensor body. The sensor may also include fluorescent indicator monomers distributed throughout and co-polymerized with the porous sensor graft material that generate signal indicative of the level of fluorescence in the indicator graft. The sensor may also include a radiation source (e.g. an LED), and a photosensitive detector element. An example of this is disclosed in U.S. Pat. No. 7,553,280, which is incorporated herein by reference. The co-polymerized indicator monomers, which can be referred to as indicator macromolecules, are formulated to create a porous sensor graft, with recognition monomers of the graft located throughout the porous copolymer graft material. The sensor body, alternatively referred to as a sensor core, may be formed from a suitable, optically transmissive polymer material with a refractive index sufficiently different from that of the medium in which the sensor will be used, such that the polymer can act as an optical wave guide. In one embodiment, the sensor may also have a power source to power the radiation source as well as an active or a passive means of data telemetry that can wirelessly convey a signal, based on the photosensitive detector, to an external receiver. An example of this is disclosed in U.S. Pat. No. 7,800,078, which is incorporated herein by reference. The sensor body may completely encapsulate the radiation source and photosensitive detector, as well as other electronic equipment, creating a self-contained device. In some embodiments, the porous sensor graft and indicator macromolecules are only located within a certain region on the surface of the sensor body.

In various embodiments of the invention, the specific composition of the porous sensor graft and the indicator monomers may vary depending on the particular analyte the sensor is to be used to detect, and/or where the sensor is to be used to detect the analyte. Preferably, the porous sensor graft, which can comprise pores of varying size generally referred to as macro-pores or micro-pores, facilitates the exposure of the indicator macromolecules to the analyte, and the optical characteristics of the indicator macromolecules (e.g., the level of fluorescence of fluorescent indicator macromolecules) are a function of the concentration of the specific analyte to which the indicator molecules are exposed. The pores of a sensor graft are generally of sufficient size to allow for the diffusion of a specific analyte through the sensor graft. In a preferred embodiment, the porous membrane structure of the sensor graft, and the size of the macro-pores (about 1 micron on average), creates a light scattering effect which provides an approximate 78% increase in signal relative to a clear non-scattering polymer formulation. This light scattering increases the overall efficiency of the system and gives the graft a white appearance.

Fluorescent molecules may be used in diagnostics as tags and probes when linked to antibodies or other molecules, and can be configured at a molecular level to be used as chemical and biochemical active indicators specifically designed to detect certain analytes, for example, glucose. Fluorescent sensors using an anthrylboronic acid-containing compound can be used as a fluorescent chemosensor for signaling carbohydrate binding, including the binding of glucose and fructose. Fluorescent molecules are susceptible to degradation, where they lose fluorescence intensity (or brightness) over time by often variable rates of oxidation. The oxidation may be commonly associated with photobleaching, (i.e. photo-oxidation), or with various reactive oxygen species within the local environment of the fluorescent molecule. Inside a living body, normal reactive oxygen species are potential oxidants and can include those involved in typical healthy healing reactions such as hydrogen peroxide, hydroxyl radicals, peroxynitrite, superoxide, and others. Inside a living system there are also specific enzymes called oxygenases for the specific purpose of oxidation in the breakdown of molecules. An adverse result of reactive oxygen species or oxygenase activity on a fluorescent molecule is typically loss of fluorescence. In the case of an indicator molecule, or a passive tag, probe, or label, the useful life and sensitivity of the device, or diagnostic, is limited, or may be rendered completely ineffective by oxidative degradation of fluorescent signal.

A source of ROS in the interstitial fluid (ISF) may be from neutrophils, which are not normally within ISF except when responding to injury. Neutrophils are typically within the interstitial space for a limited amount of time in response to injury in order to conduct their particular repair and protection functions. Neutrophils release highly reactive oxygen species which serve to oxidize and break down any damaged tissue and any foreign material to permit the regeneration/repair to complete. As seen in FIG. 1A, these reactive oxygen species can also damage the implanted device, material, or sensor by attacking key functional components such as materials and/or chemical indicators that may be susceptible to oxidation.

Preferred indicator monomers used in embodiments of the invention include those described in U.S. Patent Application Publication No. 2007/0014726 which are designed to be resistant to oxidation damage from reactive oxygen species. However, one of ordinary skill would recognize that many types of indicators may be used, particularly those described in the patents and publications referred to above. In a preferred embodiment, the indicator comprises a phenylboronic acid residue.

Preferred indicator monomers used in embodiments of the invention may also include those described in U.S. Pat. No. 7,851,225 which are designed to include an electron withdrawing group in order to reduce the susceptibility to oxidation of the indicator molecules. In embodiments of the invention, indicator molecules containing an aryl boronic acid residue may be made more resistant to oxidation by adding one or more electron-withdrawing groups to the aromatic moiety which contains the boronic acid residue, thus stabilizing the boronate moiety. It will be understood that the term "aryl" encompasses a wide range of aromatic groups, such as phenyl, polynuclear aromatics, heteroaromatics, polynuclear heteroaromatics, etc. Non-limiting examples include phenyl, naphthyl, anthryl, pyridyl, etc. A wide range of electron-withdrawing groups is within the scope of the invention, and includes, but is not limited to, halogen, cyano, nitro, halo substituted alkyl, carboxylic acid, ester, sulfonic acid, ketone, aldehyde, sulfonamide, sulfone, sulfonyl, sulfoxide, halo-substituted sulfone, halo-substituted alkoxy, halo-substituted ketone, amide, etc., or combinations thereof. Most preferably, the electron withdrawing group is trifluoromethyl. In embodiments of the invention, the electron withdrawing groups of the indicator molecules occupy the $R_1$ and/or $R_2$ positions in either of the specific chemical structures of the indicator molecules shown below:

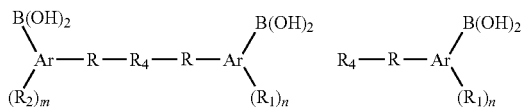

wherein each "Ar" is an aryl group; each R1 and R2 are the same or different and are an electron withdrawing group; "m" and "n" are each independently integers from 1 to 10; R4 is a detectable moiety; and each R is independently a linking group having from zero to ten contiguous or branched carbon and/or heteroatoms, with at least one R further containing a polymerizable monomeric unit. In a particularly preferred embodiment, the indicator comprises one or more of the compounds depicted in FIGS. 2A and 2B. It will also be understood from the above definition that the indicator monomer compounds and detection systems may be in polymeric form.

Figures 1, 2A:
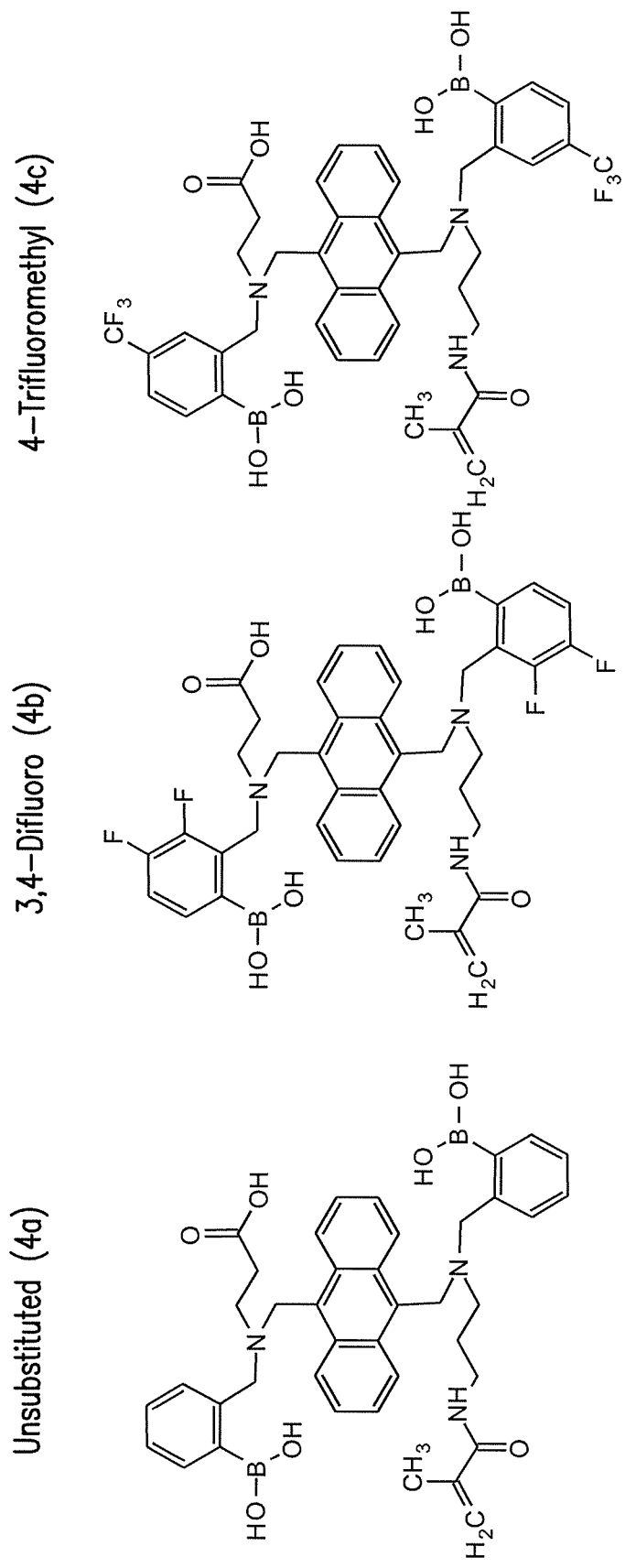
FIGS. 2A and 2B contain illustrations of examples of preferred indicator monomers for use in combination with hydrophilic co-polymers in accordance with embodiments of the present invention.
Figures 2, 2A:
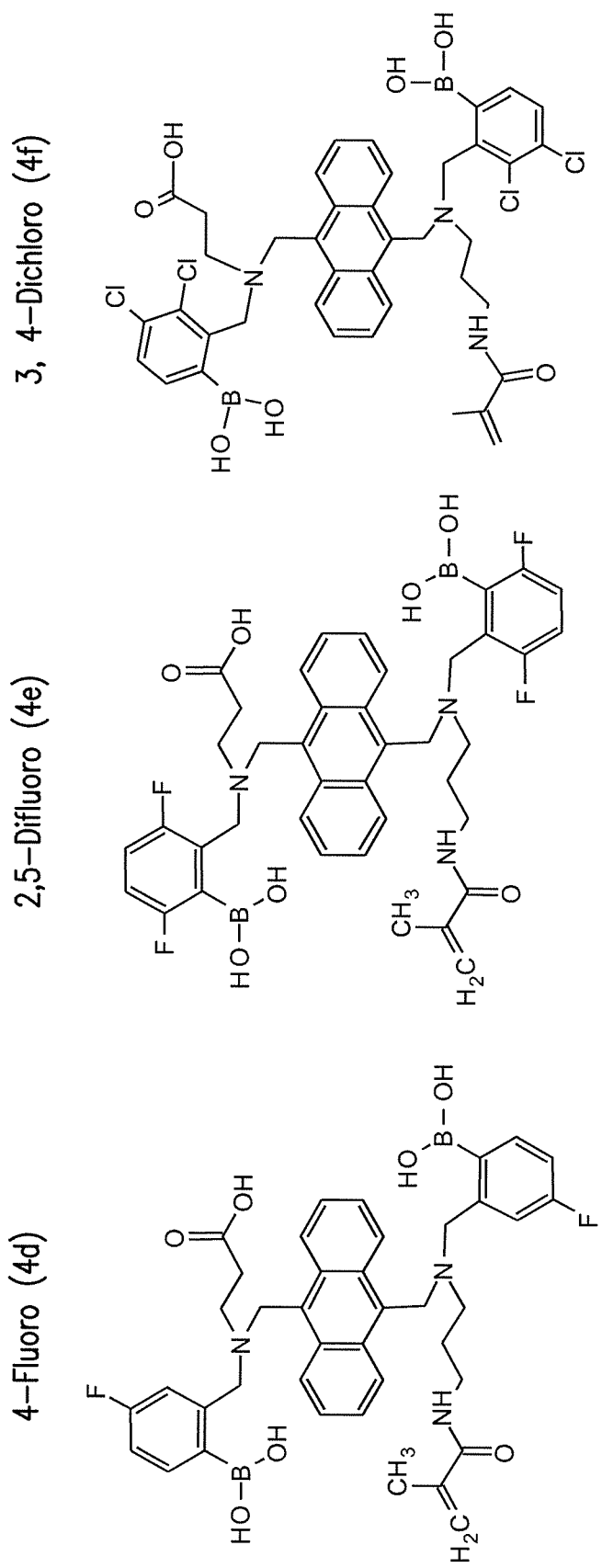
Figures 2, 2A, 3:
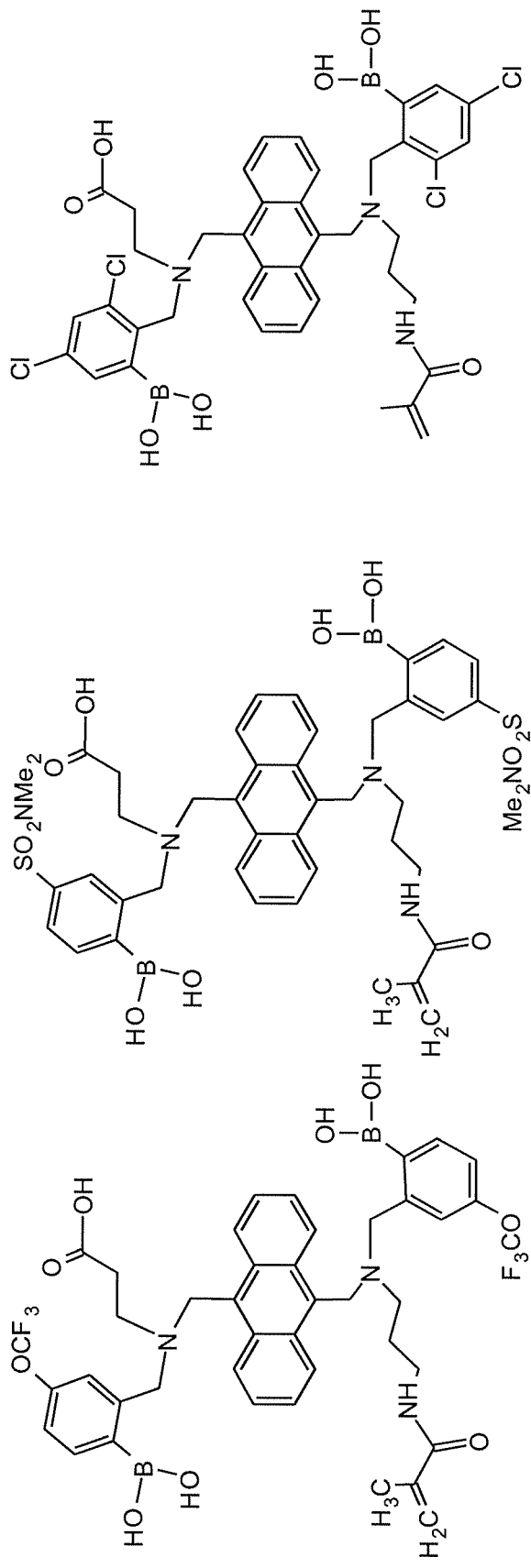
FIG. 3 is a graph showing loss of signal over time, due to reactive oxygen species (ROS), from three glucose sensors which were not treated according to an embodiment of the invention, following implantation in a living body.
Figures 1, 2B:
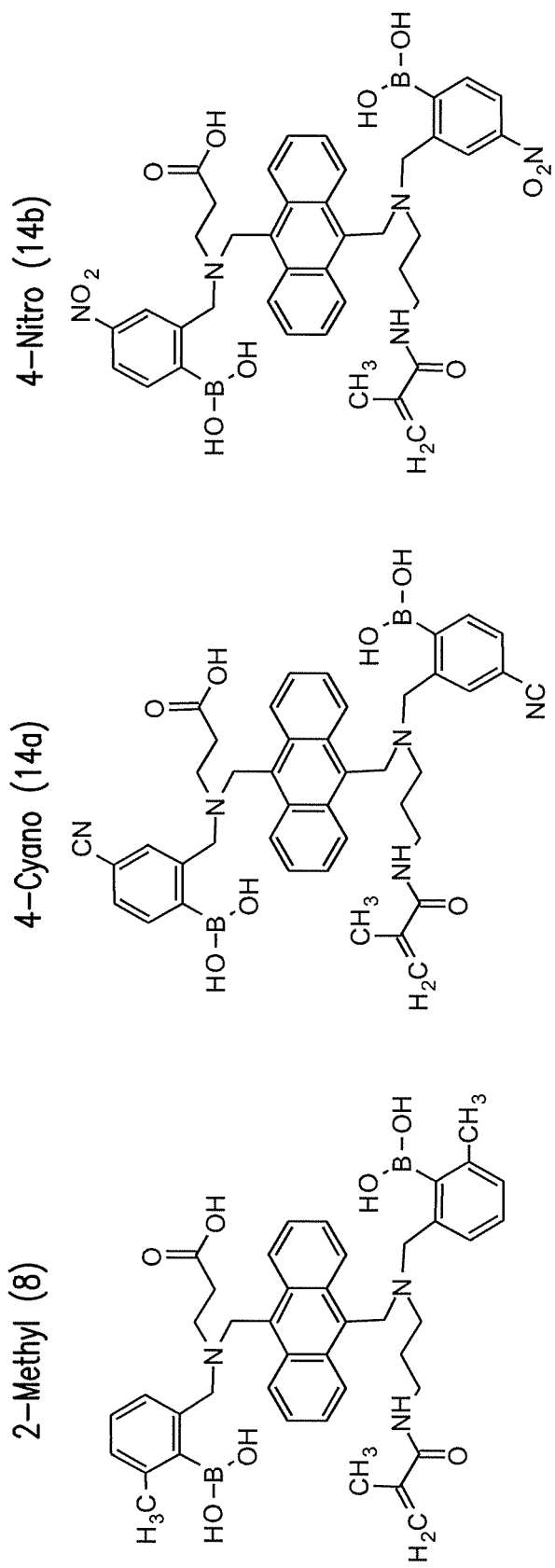
Figure 3:
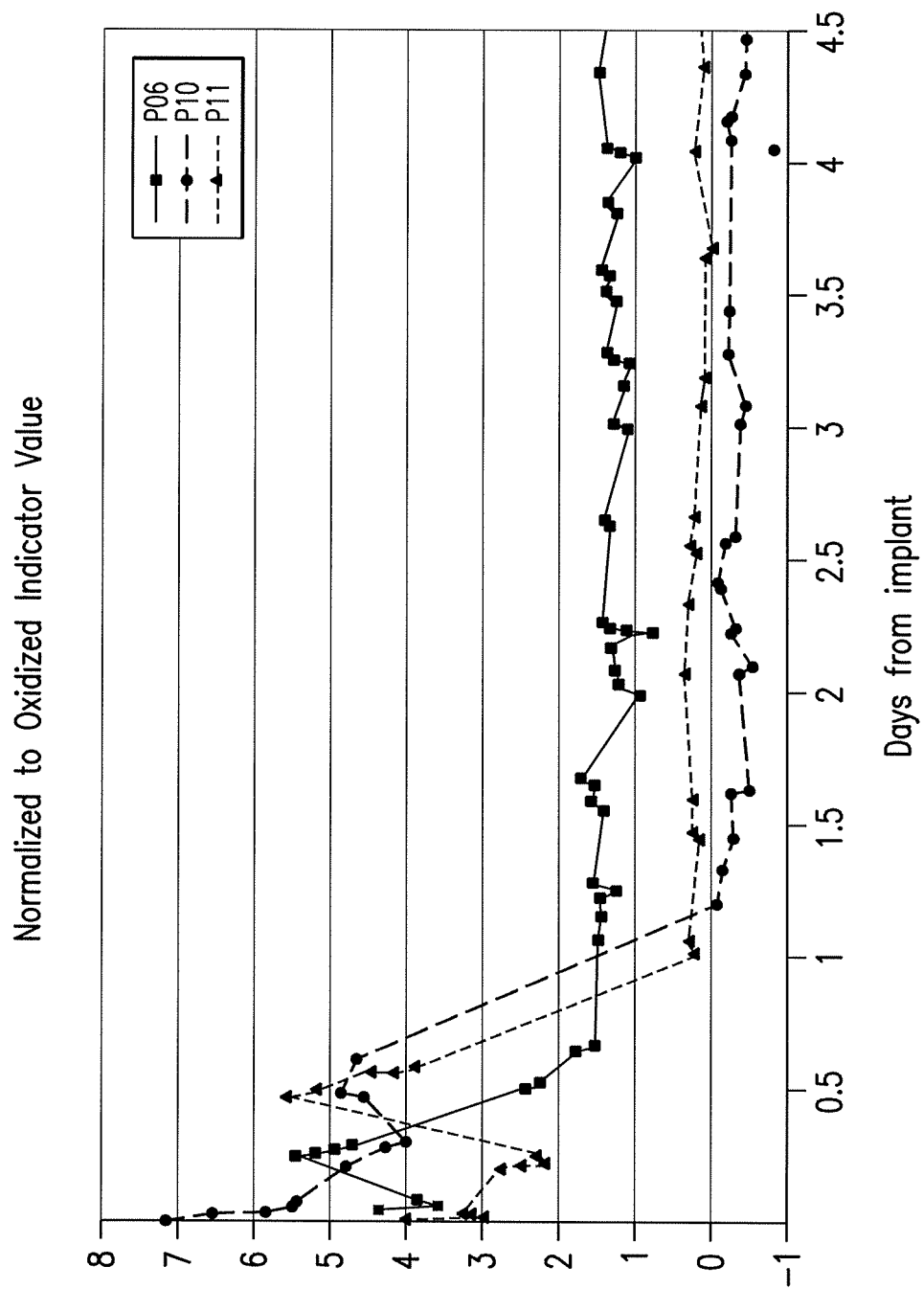

It should be understood that the invention described herein can protect any indicator, and is not limited to the preferred structures detailed in FIGS. 2A and 2B. Other materials and biologics that are put into a body may also be damaged by oxidation, particularly from oxidation due to ROS. Such other materials could be absorbance type indicators, proteins, molecules, orthopedic implants, cosmetic implants, pacemaker wires, etc. As long as the indicator or structure is susceptible to oxidation by peroxides/ROS, the invention described herein will protect such indicators or structures.

An implantable device requires a breach of the skin of some size simply to permit insertion of the device. In one embodiment of the present invention, a sensor is implanted through the skin in a procedure to place it within the subcutaneous space between muscle and dermis. Mechanical damage occurs to local and adjacent tissue as a result of the foreign body intrusion, even for the smallest and most biocompatible devices. This is because one must first penetrate the skin, and then must displace tissue to create a pocket or space where the device will be deposited and remain in place to execute its intended in vivo function. The relative biocompatibility of the sensor itself, other than its relative size and displacement, does not influence the minimal damage that is imposed on localized tissue in order to put the sensor or device into place. As a result of foreign body intrusion and localized tissue damage, an immediate and normal inflammation cascade commences within the host in direct response to the intrusion for the purpose of protecting the host, and immediately begins a repair process to correct the mechanical damage of intrusion, i.e. the wound begins to heal.

It is observed that when a sensor is placed into an animal, and even more acutely within a human, there is a near immediate biological response, and a damage inflicted on the extended performance of the sensor by the body as a direct result of inflammation. The net result of the damage from inflammation reaction is to shorten the useful life of the device, for example by diminishing signal strength. For other devices, the reduction in useful life could be measured in terms of response fouling, reducing mechanical strength, electrical or mechanical insulation properties, surface erosion (which can affect biocompatibility), or according to other measurable properties.

Inflammation response is composed in part by a transient condition occurring in direct response to an injury. There is necessarily a minor tissue injury as a result of implanting a device and it has been observed that particular aspects of the inflammation response associated with ROS can negatively affect an implanted device. Further, after the transient period of healing, although the inflammation condition surrounding the sensor significantly subsides, there is a chronic low-level foreign body response to an implanted device.

Figure 1B:
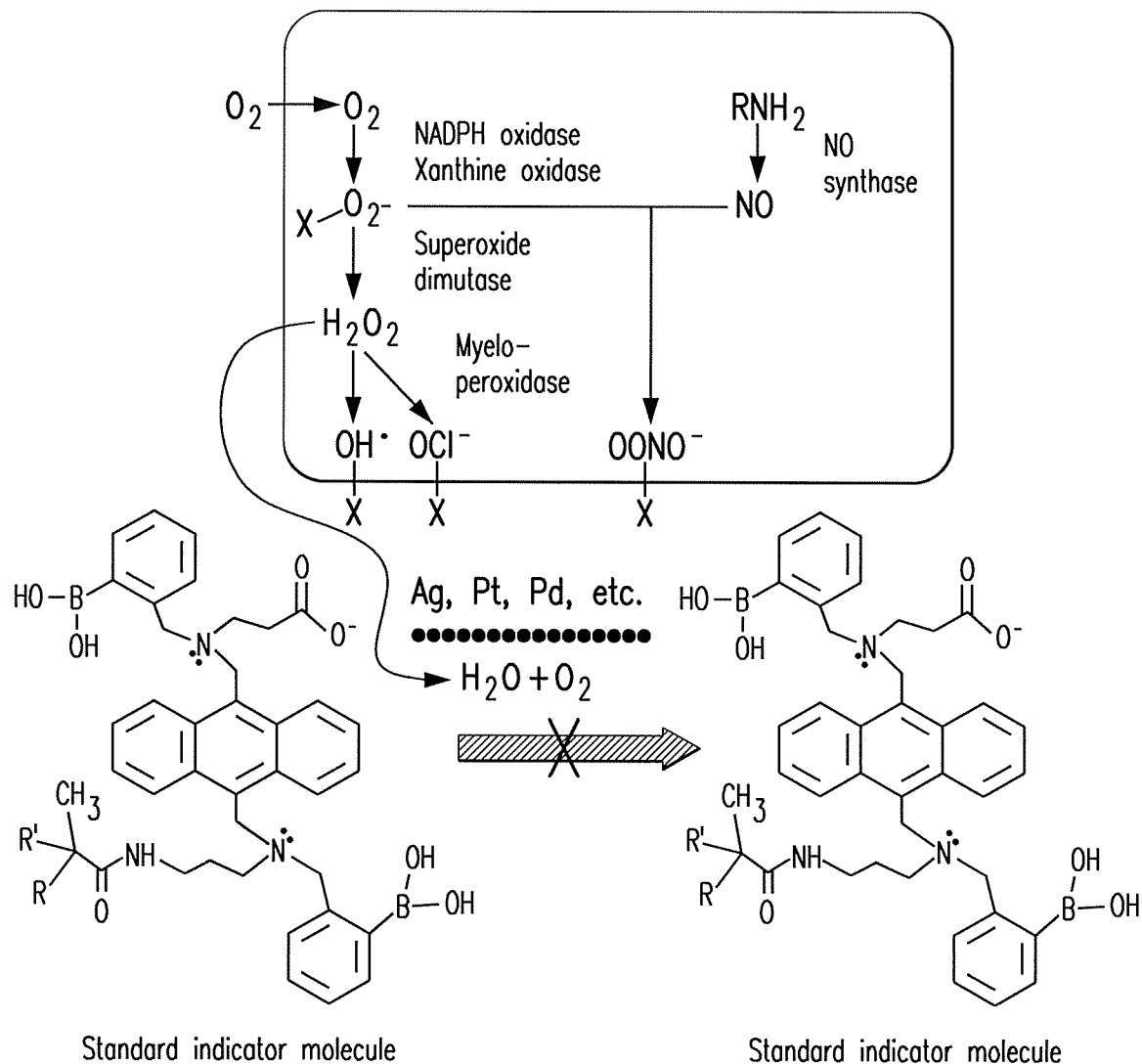
FIG. 1B is an illustration of the chemical reaction where a —B(OH)$_2$ recognition element of a glucose indicator is not oxidized by in vivo reactive oxygen species (ROS) because the presence of silver, palladium, and/or platinum catalyzes the decomposition of hydrogen peroxide before a —B(OH)$_2$ recognition element can be oxidized.

A solution to the above-referenced problems is to apply a material, structure, and/or a coating on or around the surface of the implanted device that decomposes the ROS generated locally in the region of the implant. Once a device is implanted, the material, structure, and/or coating provides a chemical barrier against ROS entering the porous sensor graft, thus preventing where ROS can attack the indicator system via oxidation, as illustrated in FIG. 1B.

In embodiments of the invention, the material, structure, and/or coating may include physiologically compatible metals or metal oxides that are capable of catalyzing the decomposition of ROS (particularly hydrogen peroxide), such as, for example, silver, palladium or platinum, or their oxides, that are sufficiently non-toxic within an in vivo environment. When the physiologically compatible metals are embodied as a coating in embodiments of the present invention, the coating may be applied to the sensor material in any suitable fashion, such as by sputter deposition. The thickness of the material, structure, and/or coating can vary widely, for example, from about 0.5 nm to about 2.5 mm. In further embodiments of the invention, the thickness of the material, structure, and/or coating can be from about 1 nm to about 20 nm thick. In yet further embodiments of the invention, the thickness of the material, structure, and/or coating can be from about 3 nm to about 6 nm thick.

FIG. 3 is a graph illustrating an example of normalized signal loss as a result of biological response to device implantation, particularly the presence of ROS, where the signal is from implanted glucose sensors. The data in FIG. 3 were obtained from three sensors, implanted into three different humans (identified as P06, P10, and P11), within the subcutaneous space in the dorsal wrist area. Following the completion of the procedure, an external watch reader was placed over the sensor to allow data communication between the sensor and external reader. Signal data were taken from the sensor over four days. It can be seen from FIG. 3 that a very rapid and significant signal drop occurs within the first day following the implant procedure (the procedure itself requires approximately 5 minutes). On the normalized scale, the signal in two of the sensors dropped by effectively 100% after twenty-four hours while the signal from the third sensor dropped by about 90% after twenty-four hours. This signal drop is undesirable because it shortens the overall useful life of the implant.

Embodiments of the present invention address the oxidation mechanism by which the ROS associated with inflammation reaction can damage a sensor implant placed within the interstitial space or anywhere that ROS may be present. Particularly, embodiments of the invention address the loss of signal by oxidation of indicator macromolecules, where the oxidation is caused by ROS. Analysis of sensors explanted from humans (and animals) shows specific and definitive evidence of reactive oxygen species attack. In the context of the present invention, an explanted sensor is a sensor (or generally any foreign object which is not biological tissue) which has been implanted into a living body and subsequently removed from that body. An explanted sensor may possess biological material that remains attached to the explant after extraction from the living body. The oxidants potentially associated with wound healing include hydrogen peroxide, superoxide, hypochlorite, peroxynitrite, and hydroxy radical as produced from local repair cells migrated to the site in response to injury. The specific oxidation reaction damage from ROS inflicted on the indicator macromolecule, which in embodiments of the invention operates as a glucose sensor, is shown in FIG. 1A.

FIG. 1A represents the in vivo ROS oxidative deboronation reaction of one glucose indicator molecule (monomer) that may be useful in connection with the present invention, and shows that as a direct result of ROS produced by the neutrophil repair cell mechanism, the boronate recognition element of the indicator system is converted to a hydroxyl group. The conversion of the standard indicator molecule to the in vivo altered indicator molecule, where the boronate recognition element of the indicator system had been oxidized to a hydroxyl group, causes a total loss of activity (specifically, fluorescence modulation as affected by glucose concentration) in the molecule. The critical bond energies in the reaction as shown in FIG. 1A are: C—C=358 kJ/mol; C—B=323 kJ/mol; and B—O=519 kJ/mol. These bond energies indicate that the carbon-boron bond, having the lowest bond energy, is most readily susceptible to attack and cleavage by oxidation. This analysis is confirmed by an Alizarin Red assay (negative for boronate), and additionally from a Gibbs test (positive for phenol) on an explanted sensor from extended animal testing. The loss of boronate from the indicator molecule directly results in loss of fluorescent signal modulation.

As stated above, ROS driven oxidation is a result of normal healing inflammation resulting from the stimulus of implanting the sensor under the skin and the attendant disruption and small damage to localized tissue. When the indicator macromolecule includes one or more boronic acid recognition elements, ROS driven oxidation causes deboronation, resulting in a loss of signal from the indicator macromolecule, thereby shortening the useful life of a sensor. ROS driven oxidation may also shorten the useful life of other similarly susceptible devices or materials. Hydrogen peroxide has been identified as the most likely ROS species that oxidizes the indicator macromolecule of the implant.

However, the decomposition of hydrogen peroxide into oxygen and water is catalyzed by metallic silver as follows:

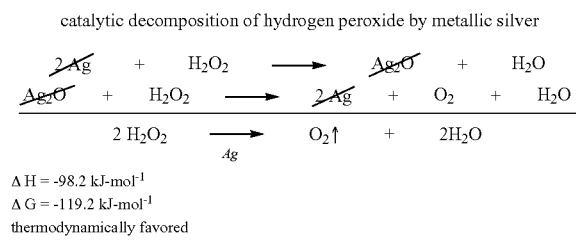

catalytic decomposition of hydrogen peroxide by metallic silver

2Ag + H$_2$O$_2$ → Ag$_2$O + H$_2$O
Ag$_2$O + H$_2$O$_2$ → 2Ag + O$_2$ + H$_2$O

2 H$_2$O$_2$ →$_{Ag}$ O$_2$↑ + 2H$_2$O

ΔH = -98.2 kJ·mol$^{-1}$
ΔG = -119.2 kJ·mol$^{-1}$
thermodynamically favored

Experiments, as described below, were conducted to determine how metallic silver could be installed or configured onto or within a sensor according to an embodiment of the invention in such a way as to protect the indicator graft by decomposing hydrogen peroxide faster than the peroxide could destroy the in vivo functionality of the sensor. Additionally, other metals, including palladium and platinum, were studied for similar activity against hydrogen peroxide and incorporation with a sensor according to an embodiment of the invention. FIG. 1B represents the in vivo protection of one glucose indicator molecule that may be useful in connection with the present invention from ROS driven oxidative deboronation reaction due to the presence of metals that catalyze the decomposition of hydrogen peroxide in accordance with embodiments of the present invention. Further, oxides of metals that catalytically decompose hydrogen peroxide may be suitable for embodiments of the invention.

An embodiment of the invention is an implantable device that includes a protective layer which protects the device from the effects of ROS driven oxidation. In embodiments, the device can be a sensor at least partially encased with a porous sensor graft, where the porous sensor graft can have indicator macromolecules embedded within the graft that are sensitive to an analyte of interest. In preferred embodiments, the indicator macromolecules can be sensitive to the presence of glucose. In embodiments, the protective layer is comprised of a metal that catalyzes the breakdown of ROS before ROS can react with any other components of the implantable device. In some embodiments, the metal of the protective layer is comprised of silver, platinum, palladium, manganese, and/or alloys or gold-inclusive alloys thereof. In some embodiments, the protective layer can be in the form of a wire, mesh, or other structural encasement wrapped around at least a part of the device. In other embodiments, the protective layer can be in the form of a coating sputter-deposited on at least a part of the device. These non-limiting embodiments are used as exemplary embodiments as set forth below.

Figure 4A:
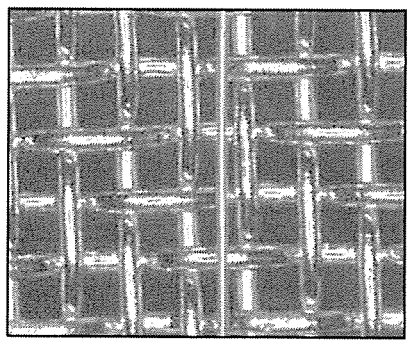
FIG. 4A is a picture of silver mesh used to deactivate hydrogen peroxide in accordance with an embodiment of the present invention.
Figure 4B:
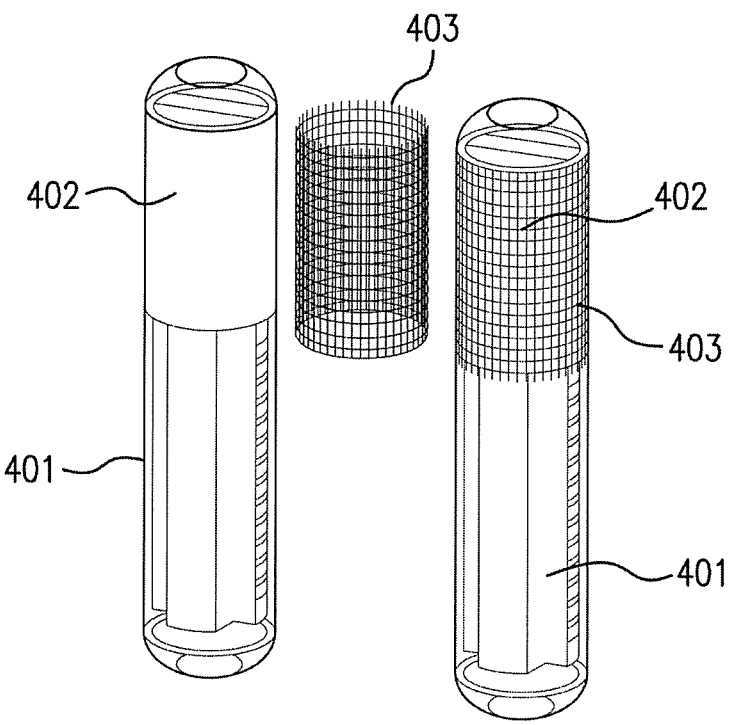
FIGS. 4B and 4C are illustrations of designs for a mesh, according to an embodiment of the invention, that is configured to fit around an implantable sensor.
Figure 4C:
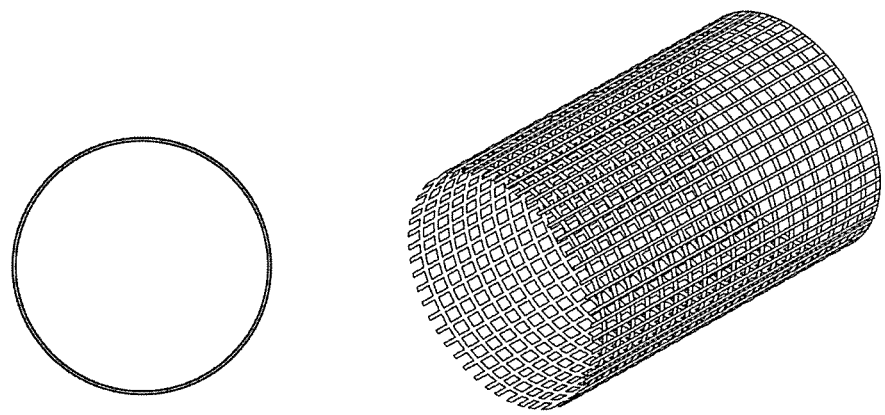

In one embodiment of the invention, metallic silver is placed between the sensor graft and an external environment such that any hydrogen peroxide would be required to diffuse through a porous catalytic barrier, such as a mesh, and thus be decomposed into water and oxygen prior to any reaction with the indicator molecules. The efficacy of silver for decomposing hydrogen peroxide was tested using 180× 180 micron pure silver mesh, as seen in FIG. 4A. (The value used for the mesh refers to wires/inch. FIG. 4A also shows a 25 micron thick (diameter) gold wire along with the silver mesh to provide scale.) FIG. 4B is an illustration of a mesh 403 and how a mesh 403 would fit around the sensor 401, wherein the sensor 401 has a region of porous sensor graft 402, according to an embodiment of the invention. FIG. 4C is a further illustration of a side and end views of a mesh used in accordance with an embodiment of the invention.

To test the catalytic effect of a silver mesh on hydrogen peroxide, four samples (Samples A, B, C, and D) containing xylenol orange were tested as set forth below. The detection is based on the oxidation of ferrous to ferric ion in the presence of xylenol orange, where a sample that does not contain hydrogen peroxide in solution appears clear and orange. When hydrogen peroxide is present in combination with xylenol orange, the solution appears purple and opaque. Sample (A) was a control which had no hydrogen peroxide added. Sample (B) contained 0.2 mM hydrogen peroxide without any silver present; the hydrogen peroxide in the sample caused the solution to be purple and opaque. Sample (C) contained 0.2 mM hydrogen peroxide with silver mesh present for thirty (30) minutes. Compared to sample (B), sample (C) was more clear and lighter in color, indicating that the amount of hydrogen peroxide in the solution of sample (C) was decreased. Sample (D) contained 0.2 mM hydrogen peroxide with silver mesh present for sixty (60) minutes. Sample (D) was orange in color and clear and appeared identical to Sample (A), the control, indicating that there was no hydrogen peroxide remaining in the solution of Sample (D).

Figure 5A:
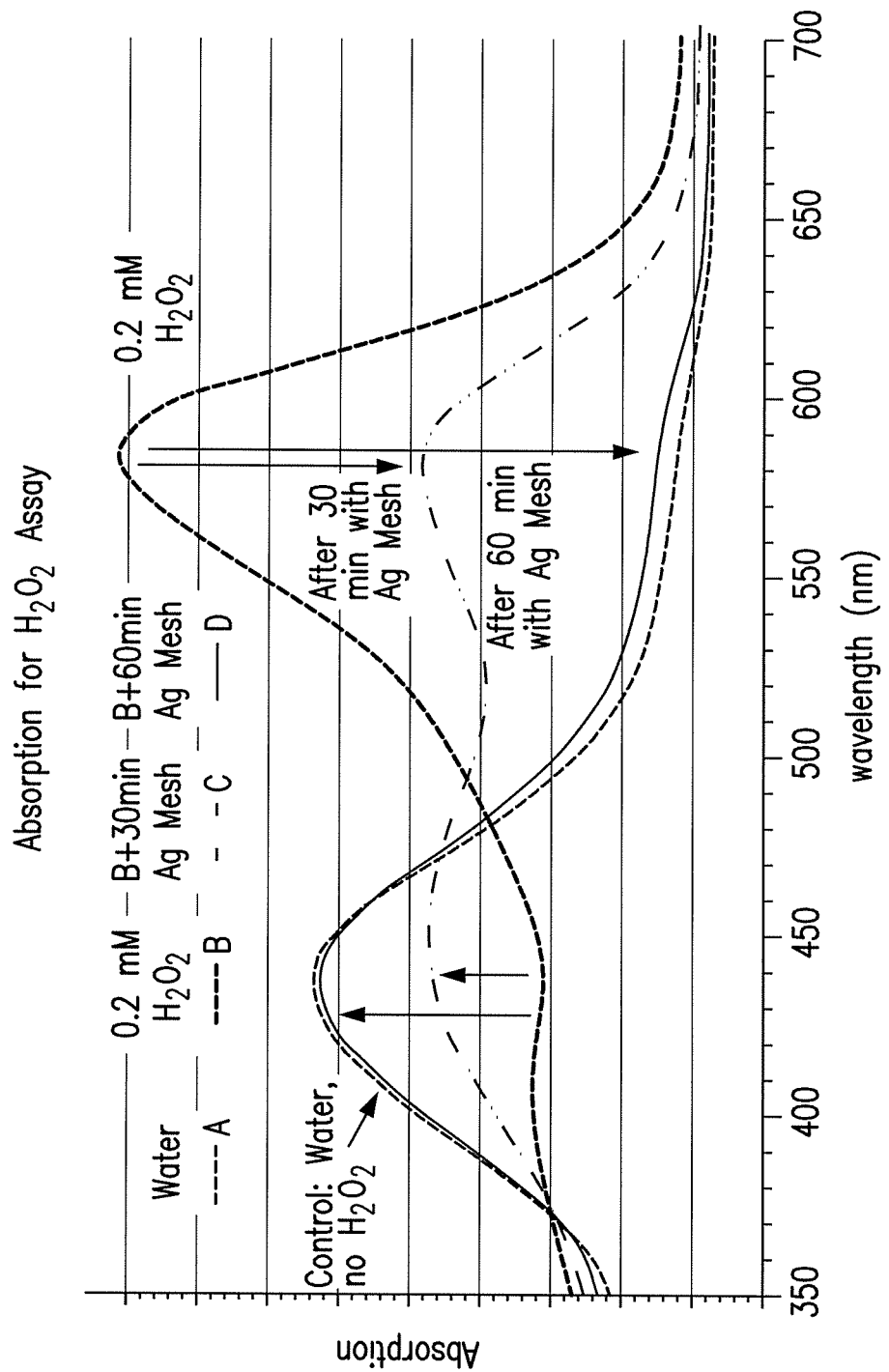
FIG. 5A is the absorption profile of four xylenol orange-based samples used to test for the detection of hydrogen peroxide.

FIG. 5A shows the absorption profile across the spectrum of visible light for Samples (A), (B), (C), and (D). Notably, the absorption profile of sample (D), 0.2 mM hydrogen peroxide exposed to silver for sixty (60) minutes, is nearly identical to the absorption profile of the control sample (A) which contained no hydrogen peroxide.

Figure 5B:
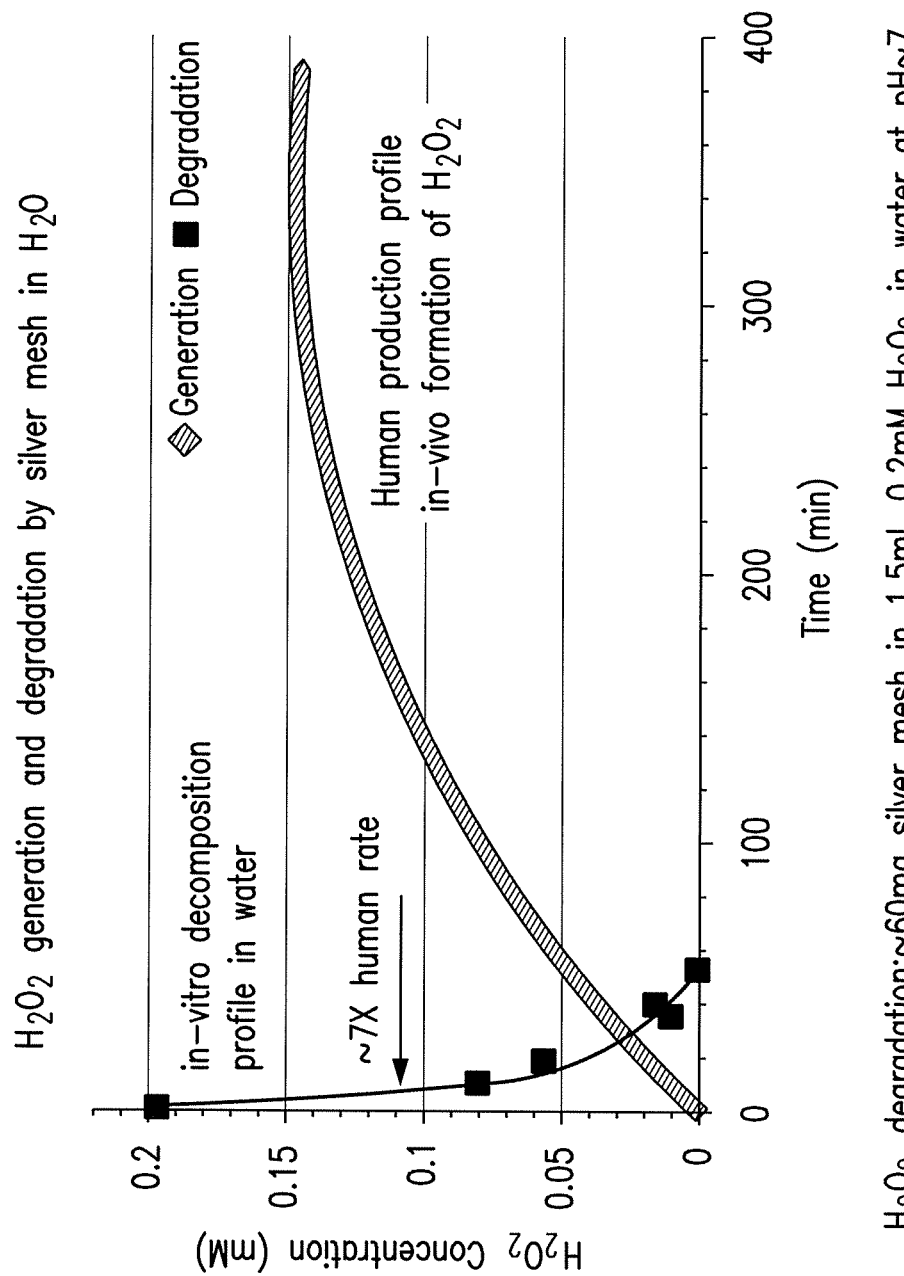
FIG. 5B is a comparison of the hydrogen peroxide production profile in vivo with the profile of hydrogen peroxide degradation by silver.

FIG. 5B shows a comparison between the in vitro decomposition profile of hydrogen peroxide by silver mesh in water and the in vivo production profile of hydrogen peroxide as measured in a human body implant site. The in vitro decomposition profile is of an about 60 mg silver mesh in 1.5 mL of 0.2 mM hydrogen peroxide in water at a pH of about 7. In comparing the two profiles, it is evident that the rate of hydrogen peroxide decomposition using a silver catalyst, such as the 180×180 pure silver mesh, is approximately seven times faster than the in vivo rate of hydrogen peroxide production, as measured in human type 1 diabetic wound healing.

The catalytic activity of silver in decomposing hydrogen peroxide into water and oxygen is so effective, that any silver used for this purpose in combination with an implantable device would still be effective even if only in close proximity to the implant. In other words, silver does not necessarily need to be bonded to or incorporated with the structure of the device. However, it is known that the in vitro catalytic activity of silver degrading hydrogen peroxide can be inhibited by chloride ions. This inhibition of silver by chloride can be referred to as silver catalyst poisoning.

Other metals, such as palladium and platinum, also decompose hydrogen peroxide at different rates and efficiencies and kinetic profiles. The inventors of the present invention have found that neither palladium nor platinum was poisoned by chloride or inhibited by high protein concentrations of serum albumin (70 mg/ml or greater). Similarly to silver, palladium and platinum also decompose hydrogen peroxide at a rate faster than the body can produce hydrogen peroxide and are effective, in close proximity to an implantable device, at preventing hydrogen peroxide from reaching and/or damaging the device. Alternatively, alloys of silver, palladium, platinum, gold or combinations or oxides thereof may be used to catalyze the degradation of hydrogen peroxide into oxygen and water. Close proximity, in the context of the present invention, is a distance close enough to allow a device and/or material to function in the intended manner. The range of distance or thickness that qualifies as in close proximity will vary, depending on the structure and configuration of the structural embodiment. Typically, the range of close proximity will be up to about 2.5 millimeters. In embodiments of the invention, the structure used to protect the sensor does not have to completely surround or encapsulate the sensor body, but only needs to be implemented to protect the indicator region of the sensor.

Samples of platinum and palladium were separately placed in solutions of 0.2 mM hydrogen peroxide at 37° C. in phosphate buffered saline (PBS) for several hours. The samples were platinum meshes and palladium coils wrapped from pure metal wire and slid over the membrane graft region of a sensor core according to an embodiment of the invention. This experiment was repeated with many different samples, with fresh hydrogen peroxide introduced in each trial. The platinum and palladium samples completely degraded the hydrogen peroxide in solution. In some embodiments of the invention, platinum and palladium are preferred metals to use in designing structures that incorporate a metal catalyst into the sensor. Such structures can be up to about 2.5 mm in thickness, measured from the surface of a device.

Figure 6A:
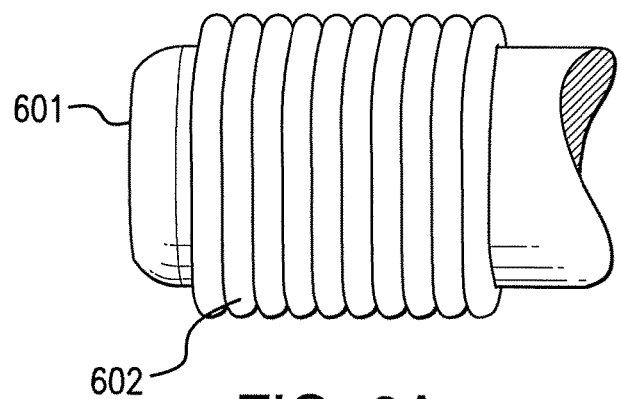
FIGS. 6A and 6B are a side and cross-sectional illustration of an embodiment of the invention where a metal wire is wrapped in a coil around a portion of an implantable sensor core.
Figure 6B:
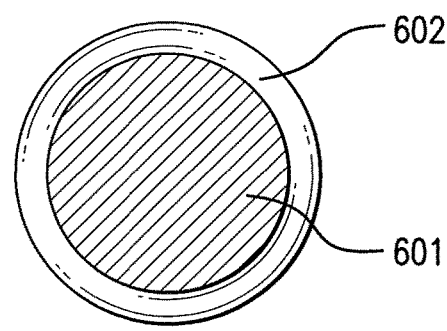
Figure 6C:
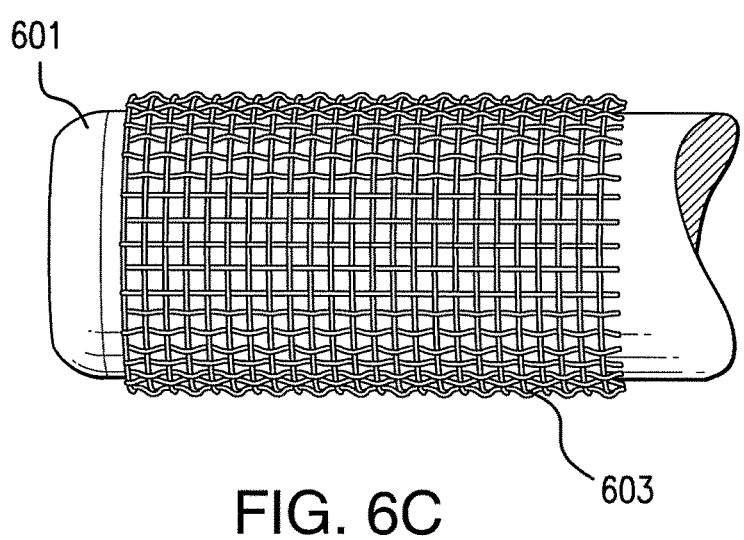
FIGS. 6C and 6D are a side and cross-sectional illustration of an embodiment of the invention where a metal mesh is fitted around a portion of an implantable sensor core.
Figure 6D:
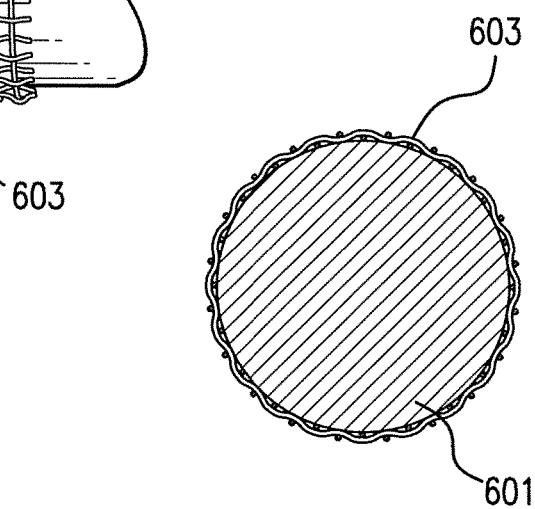
Figure 6E:
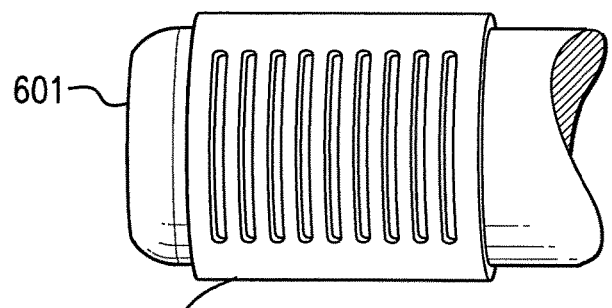
FIG. 6E is a side illustration of an embodiment of the invention where a slotted metal encasement is fitted around a portion of an implantable sensor core.
Figure 6F:
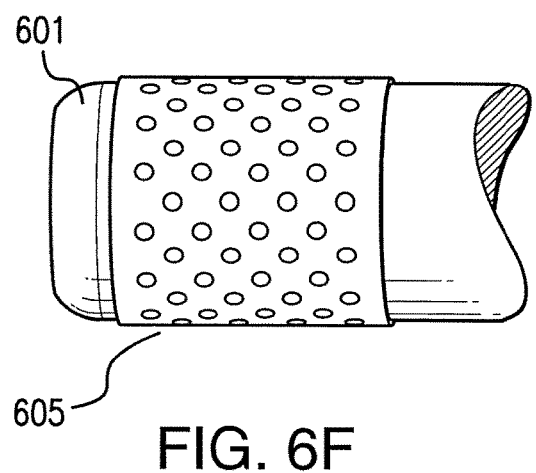
FIG. 6F is a side illustration of an embodiment of the invention where a perforated metal foil is fitted around a portion of an implantable sensor core.
Figure 6G:
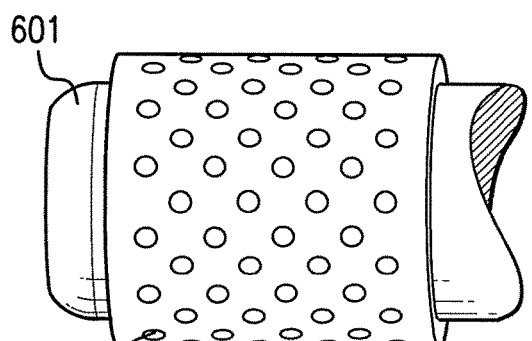
FIG. 6G is a side illustration of an embodiment of the invention where a perforated metal jacket is fitted around a portion of an implantable sensor core.
Figure 6H:
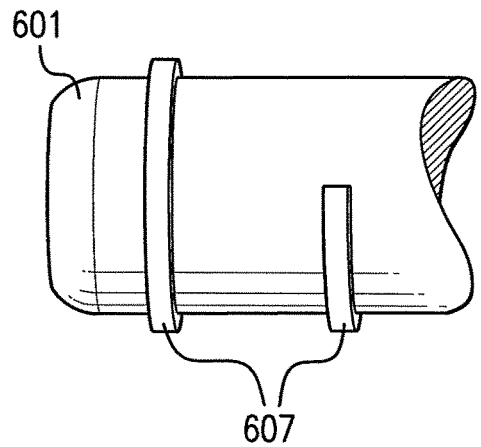
FIG. 6H is a side illustration of an embodiment of the invention where a metal ring and a metal partial ring are fitted around a portion of an implantable sensor core.
Figure 6I:
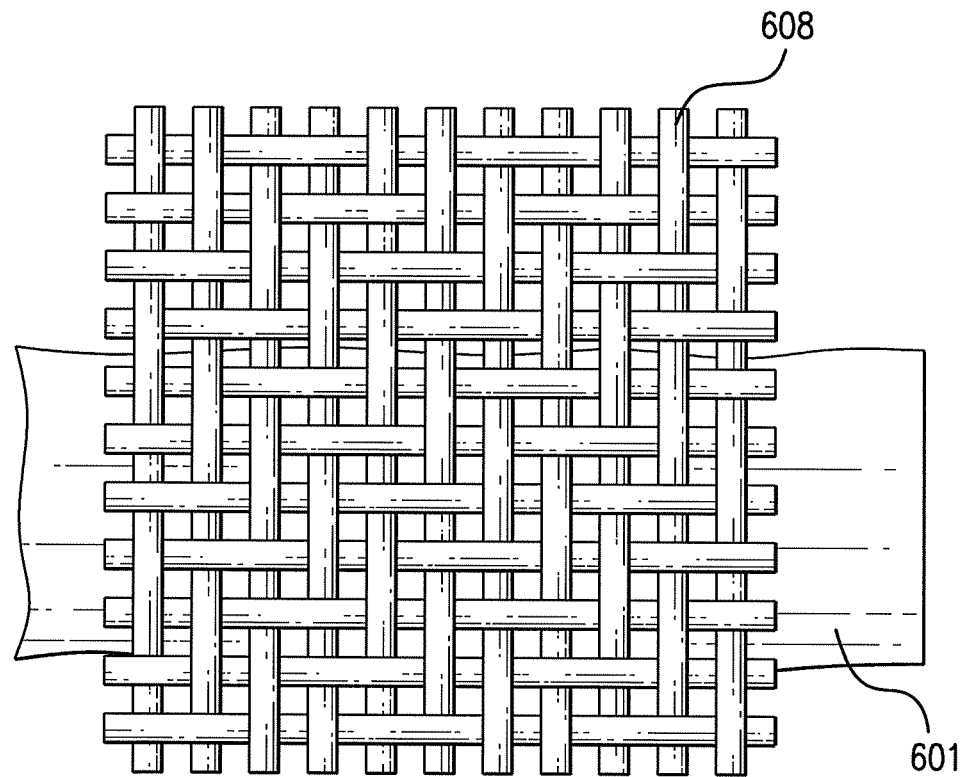
FIG. 6I is a side illustration of an embodiment of the invention where a metal weave is in close proximity to a portion of an implantable sensor core.
Figure 6J:
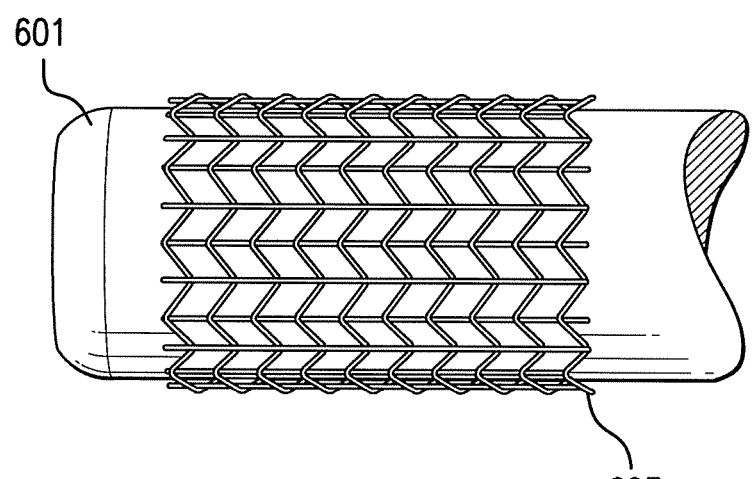
FIG. 6J is a side illustration of an embodiment of the invention where a zig-zag patterned metal mesh is fitted around a portion of an implantable sensor core.

FIGS. 6A and 6B illustrate a side and cross-sectional view of a wire 602 wound around a sensor core 601 in accordance with embodiments of the invention. FIGS. 6C and 6D illustrate a mesh 603 wound around a sensor core 601 in accordance with embodiments of the invention. In non-limiting embodiments, the wire and mesh are wrapped into coil or cylinder configurations and slipped over the sensor such that analytes, such as glucose, could diffuse between the cracks of the coils or mesh. Other structural configurations contemplated for embodiments of the invention, in addition to metal or metal oxide in a coil or mesh form, are as a perforated or slotted encasement 604 as in FIG. 6E, a perforated or slotted foil 605 as in FIG. 6F, a perforated or slotted jacket 606 as in FIG. 6G, a ring or partial ring 607 as in FIG. 6H, a weave or Dutch weave 608 as in FIG. 6I, a zig-zag patterned mesh 609 as in FIG. 6J, and other such structures made from either metal and/or metal oxide wire and/or ribbon, or other forms of material stock. These structures are designed such that hydrogen peroxide in the environment will react on the metal as the hydrogen peroxide tries to diffuse into the graft of the implantable sensor. In preferred embodiments of the invention, designs are intended to both increase the surface area of the metal exposed to the external environment and to be a diffusion layer with a sufficient density of pores, gaps, and/or perforations covering the surface of the graft of an implantable sensor, so as to protect the graft indicator macromolecules from oxidation by ambient hydrogen peroxide.

An alternative embodiment of the invention may use nanoparticulate forms of metals that catalyze the degradation of hydrogen peroxide (as disclosed herein), suspended within a porous sensor graft. In one non-limiting embodiment, formation of a porous sensor graft material may involve a gel suspension, to which nanoparticulate metals can be added. Once formed as part of a device, the porous sensor graft with nanoparticulate metals entrapped within the graft can operate to prevent ROS driven oxidation of other components of the sensor graft and device, such as indicator molecules. In embodiments of the invention, the nanoparticulate metals can be distributed evenly throughout the porous sensor graft and/or micro-localized within the graft. In an non-limiting embodiment of the invention, the nanoparticulate metals may be up to 80 nm in diameter.

While embodiments utilizing structural encasements (e.g. wire, mesh, sheath, etc.) are successful at protecting implantable devices from oxidative degradation by hydrogen peroxide, because of the very small size of implantable devices, it is recognized that such protective structures may be awkward or difficult to mechanically install onto such devices as a barrier between the graft and outside solutions (and tissue). The use of such structural encasings may also have a high cost, especially in the case of platinum and palladium materials. Edge effects, surface morphology, and fabrication quality at the small dimensions required for structures to be incorporated with an implantable device may also be issues with structural encasings. Additionally, catalysis of hydrogen peroxide occurs on the surface of the metal and, relative to the size of a hydrogen peroxide atom, the amounts of metal contemplated in structural embodiments may be orders of magnitude greater than might be theoretically required to achieve the desired decomposition of hydrogen peroxide. It is also a concern that tissue may also grow into the spaces of a coil, mesh, weave, etc. and make any potential removal of the sensor more tedious and damaging to local tissue to some extent. This does not mean to imply, however, that embodiments utilizing structural encasements are not viable and robust solutions to the above-described problems relating to ROS driven oxidation. To the contrary, they have been shown to be very effective.

In other embodiments of the invention, the protective metals may be applied to the porous sensor graft using sputter coating techniques. For example, the techniques can use sputtering targets comprising silver, platinum, palladium, manganese, gold, and alloys and/or oxides thereof. A sensor graft sputter coated with metal or metal oxide must remain sufficiently porous to allow analytes to pass through into the sensor graft, but still effectively work as a protective barrier against the diffusion of hydrogen peroxide into the sensor graft. In embodiments of the invention, the metal or metal oxide acting as a catalyst may be configured as a slightly tortuous diffusion layer between outside world and inner graft, which protects the indicator from hydrogen peroxide even at high concentrations and fast physiological production rates. The slightly tortuous diffusion layer may also be characterized as a permanently selective catalytic barrier.

Figure 7:
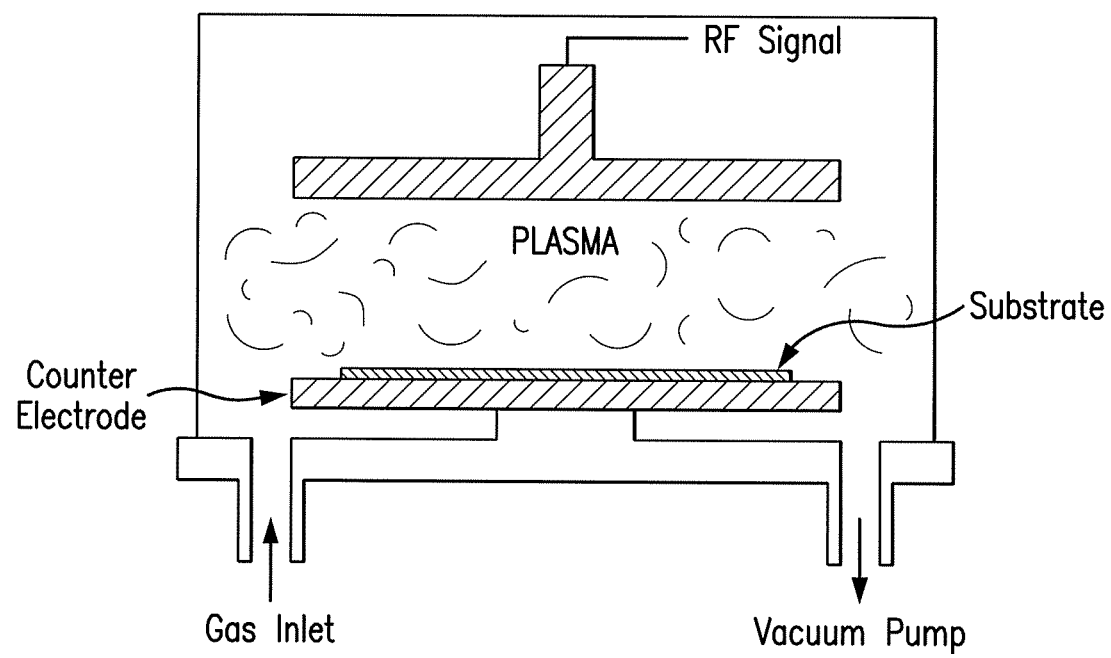
FIG. 7 is a representation of plasma sputtering of a metal onto the porous sensor graft of an implantable sensor.

Sputter deposition is a well-known method of depositing thin metal films by sputtering, i.e. ejecting, material from a metal source or "target," after which the atoms from the target deposit onto a substrate. Typically, within a vacuum sealed environment, high energy ionized gases form a plasma and are projected at a target which causes atoms of the metal target to be broken off from the target. As the metal atoms dislodged from the target deposit onto a substrate, a thin film of that metal forms on and bonds to the substrate. Depending on the gas used for projection onto the target and the composition of the target itself, the metal film that is deposited on to the substrate may be a pure metal, an alloy, an oxide, a nitride, an oxynitride, etc. FIG. 7 is a general representation of a sputter coating chamber.

Figure 8A:
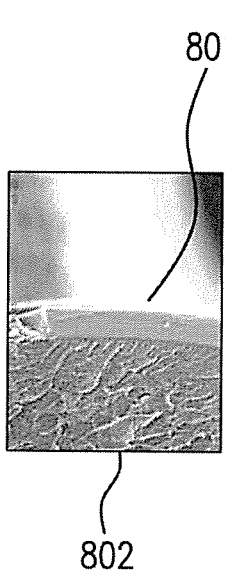
FIGS. 8A, 8B, and 8C are cross-sectional scanning electron microscope (SEM) images, at increasing magnification levels, of metallic gold sputtered onto an implantable sensor core.
Figure 8B:
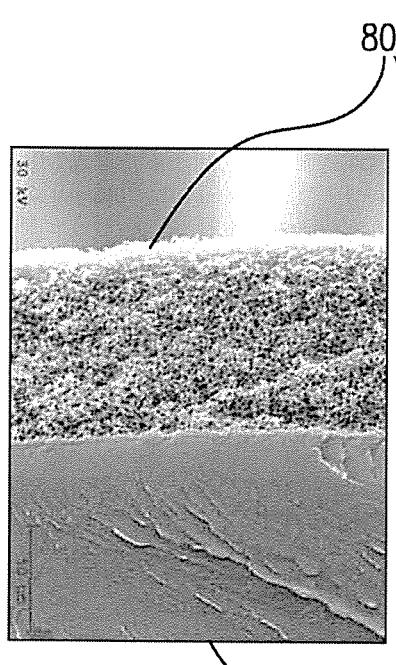
Figure 8C:
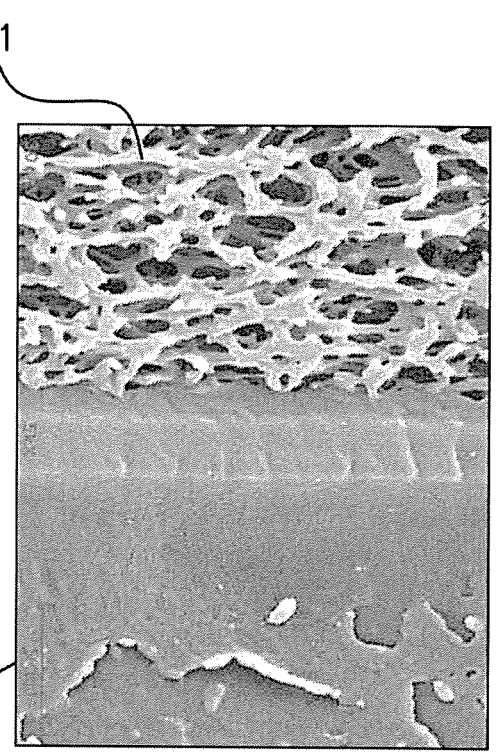

A gold target was used for the initial testing of sputter deposition onto a porous sensor graft. FIGS. 8A-C are three SEM images, increasing in magnification, of the sensor graft sputter coated with gold. The porous sensor graft material itself is normally not visible by SEM. The images in the photos are of metallic gold, which is visible under SEM, sputtered onto the surface of the hydroxyethylmethacrylate (HEMA) copolymer graft 801. Thus, these photos are only of the metallic gold shell covering the graft element surface following sputter deposition using a gold target. The sensor graft 801 used for FIGS. 8A-C was cleaved and then sputtered, such that the cross-sectional image and full depth of the graft membrane could be observed under SEM. If sputtered from outside only, then cleaved, then SEM imaged, the expected image would be a metallic porous thin layer riding atop an invisible organic graft layer below. The metallic gold layer visible in the graft region is very thin (a few nm), with a very high surface area, at least matching that of the porous graft itself. Sputter coating the graft 801 with metal does not clog or foul the macro-porosity of the graft; i.e. analytes of interest will still be able to diffuse through and interact with indicator molecules. In embodiments of the invention, the coating used to protect the sensor does not have to completely surround or encapsulate the sensor body 802, or even cover the entire portion of porous graft 801 present on a sensor, but only needs to be implemented to protect the indicator region of the sensor.

Figure 9:
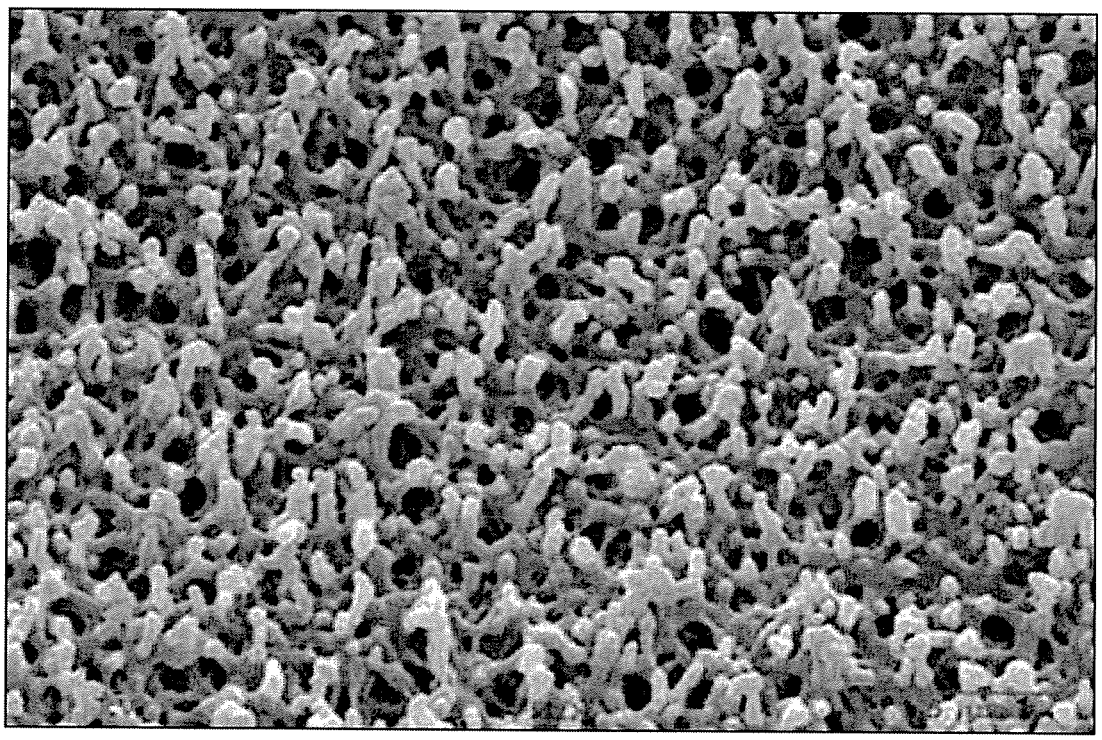
FIG. 9 is a SEM image of the outside surface of an implantable sensor core sputtered with gold.

FIG. 9 is an SEM photo from the outside surface of the graft looking inward toward the sensor body. Again, this image is not technically of the graft, but is rather an image of metallic gold sputtered over the graft, which allows the graft to be visualized by SEM. This image shows that effectively the entire surface area of the graft visible is coated with gold. Thus, it can be inferred that the surface area of exposed metal at least is equivalent to the surface area of the graft. An embodiment as described above in FIG. 6A used a 400 micron diameter palladium wire coil wrapped around the outside diameter and displayed excellent protection against hydrogen peroxide. The sputter coating of metal onto the porous sensor graft has a surface area greater than the wire coil. This implies that the protective ability of sputter coated metal on a porous sensor graft may be superior to embodiments utilizing a structural encasement of the invention discussed above.

Figure 10A:
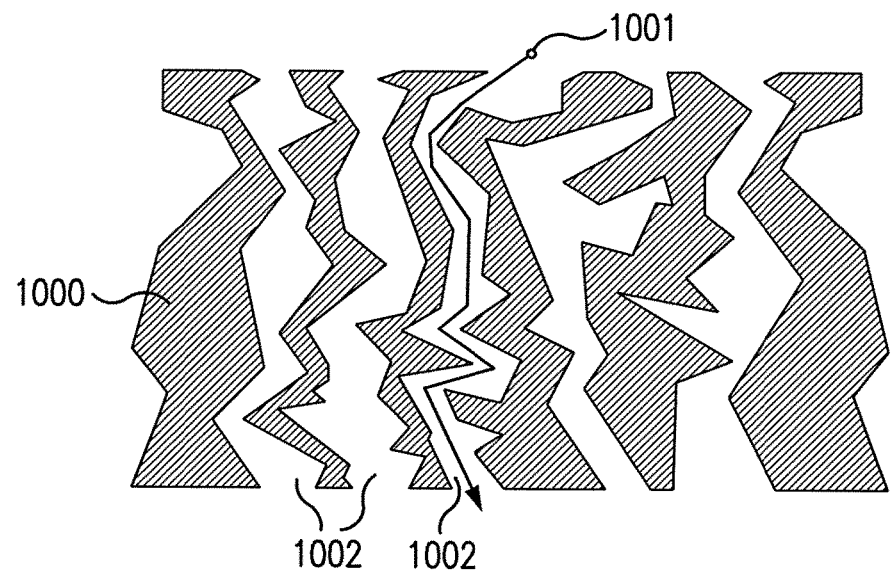
FIG. 10A is a diagram of a tortuous membrane of a porous sensor graft in accordance with an embodiment of the present invention.
Figure 10B:
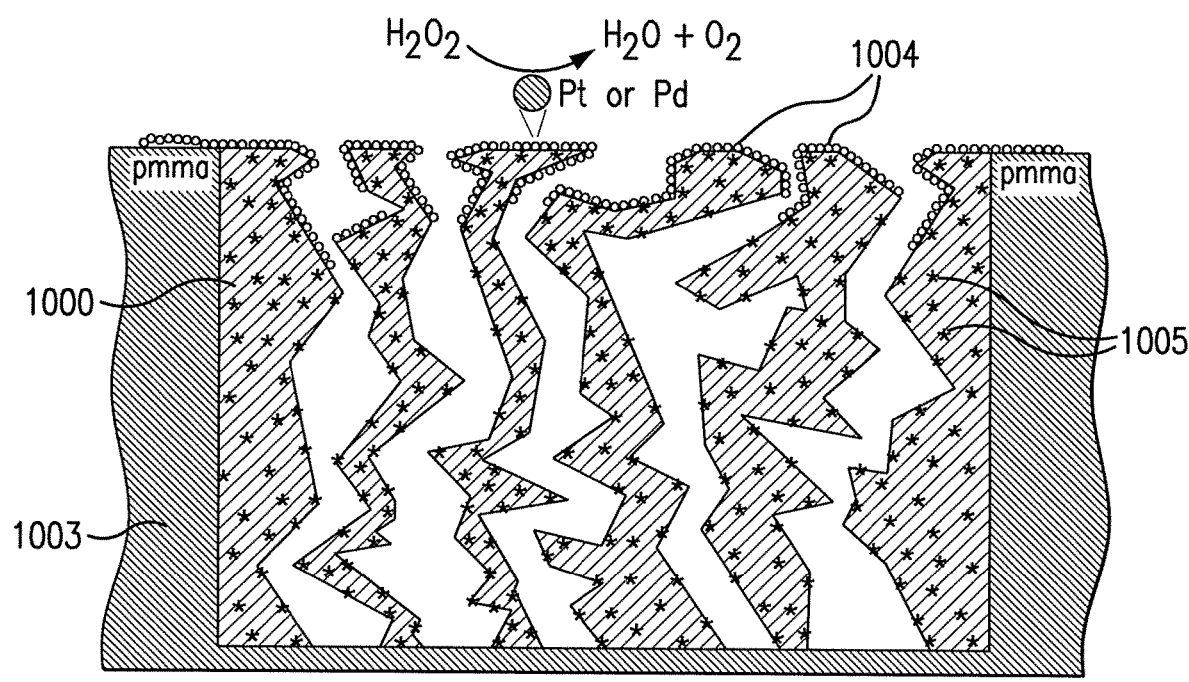
FIG. 10B is a diagram of a tortuous membrane, additionally showing indicator macromolecules dispersed throughout a porous sensor graft and sputter coated with a metal.

FIG. 10A is a representation of the tortuous membrane structure 1000 that comprises the porous sensor graft, which can be a portion of an outer structure of a sensor body 1003, in accordance with an embodiment of the invention. Any solute 1001 must follow a tortuous diffusion path 1002 to pass through and cross the membrane 1000. FIG. 10B is a representation of the tortuous membrane 1000 with a metalized surface layer 1004, with indicator molecules 1005 also represented in the porous sensor graft 1000. Although this creates a tortuous diffusion barrier, the macro-pores are still about 1 micron, and wide open without metal fouling. In embodiments, the depth of the porous sensor graft sputtered is limited to line of sight at the micro level. Metal sputtered from a target generally cannot diffuse deep into the tortuous membrane structure because the sputtered metal deposits upon impact, and thus areas below the surface that are shadowed remain uncoated, as represented in FIG. 10B. In some embodiments of the invention, the thickness of this metalized layer 1004 into the porous sensor graft may be 5 microns or less. In other embodiments, additional pressure may be introduced to the sputtering environment, magnetic fields may be used, or other methods may be used to cause the tortuous membrane 1000 to be sputtered past the point of line of sight deposition, such that the metalized layer 1004 may extend down through the full depth of the porous sensor graft. As stated above, the sensor graft remains porous after sputter deposition.

In certain embodiments of the invention, the full depth of the porous sensor graft is about 100 microns. The surface area of the porous sensor graft sputter coated with metal is expected to lose the function of any indicator molecules covered by the sputtered metal. However, in such an embodiment, if about the top 5 microns are allocated to surface metallization to provide a catalytic metal protection layer, the remaining about 95 microns of sensor graft are more than adequate to provide signal and modulation according to embodiments of the invention. There is no concern that the metal sputtered onto the graft membrane will have any negative effect on the structural integrity or function of the graft membrane. In embodiments of the invention, the thickness of the metal layer can be from about 0.5 nm to about 500 nm thick. In a particular embodiment of the invention, the thickness of the sputtered metal layer is about 1-20 nm thick. In a preferred embodiment of the invention, the thickness of the sputtered metal layer is about 3-6 nm thick.

For preferred embodiments, both palladium and platinum are generally used and commercially available sputtering targets. Either of these metals, or alloys or combinations of these metals or optionally others of the type, can be used to sputter the surface of a porous graft layer. These metals, sputtered onto a sensor graft, can construct a protective layer over the graft that will permit free diffusion of glucose (or other analytes of interest), but will also decompose hydrogen peroxide encountered at the sensor surface during wound healing and for the duration of the useful life of the sensor in vivo. In various embodiments, the entire surface of a sensor core can be sputter coated or only a portion of the sensor core can be coated.

Figure 11A:
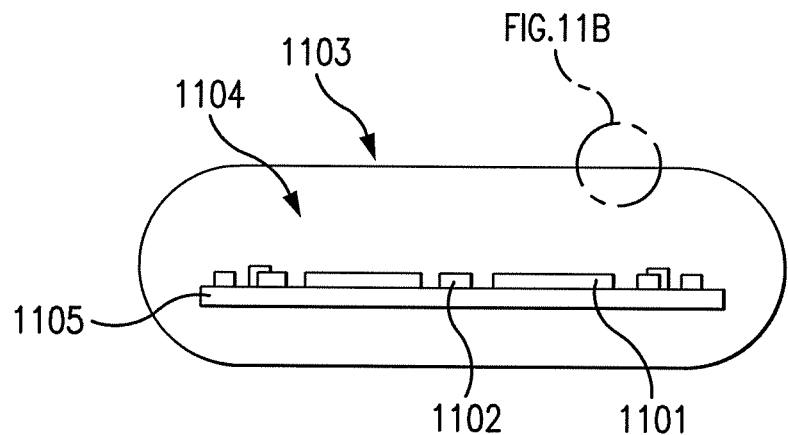
FIG. 11A is a general schematic of implant device showing an immobilization support for immobilizing indicator monomers in accordance with an embodiment of the present invention.
Figure 11B:
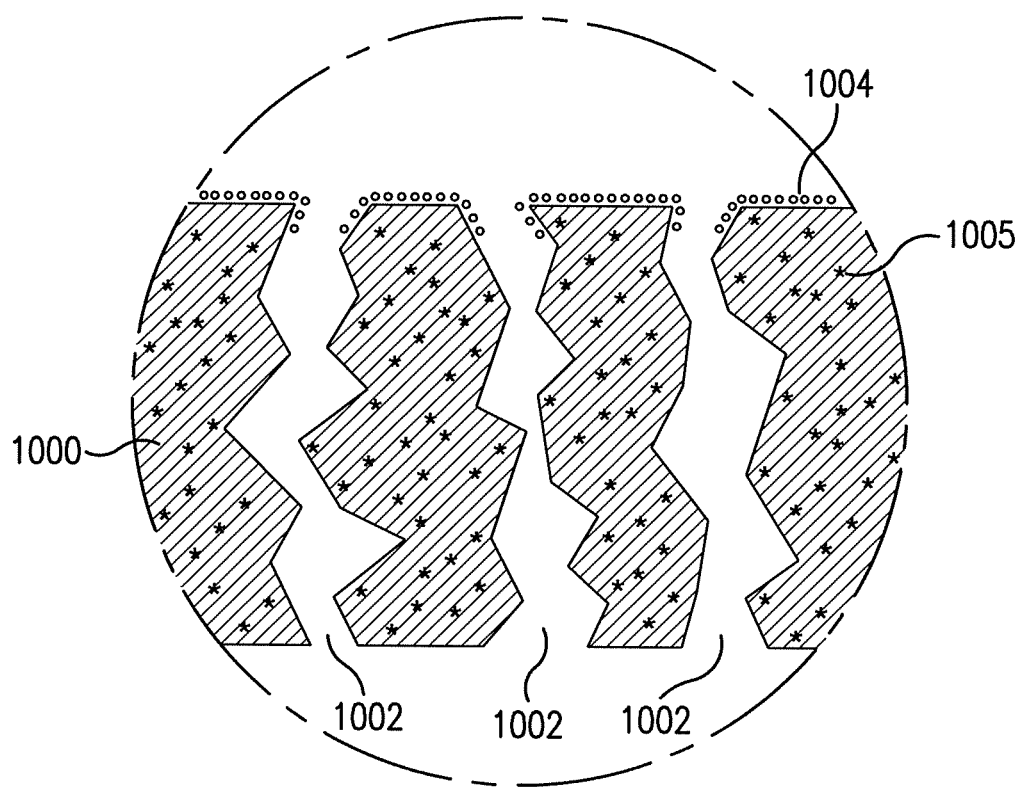
FIG. 11B is a detail of FIG. 11A, further showing the immobilization support, particularly the porous sensor graft membrane with indicator monomers integrated into the graft and a platinum barrier layer sputtered onto the surface of the porous sensor graft, and more generally, onto the device as a whole.
Figure 12A:
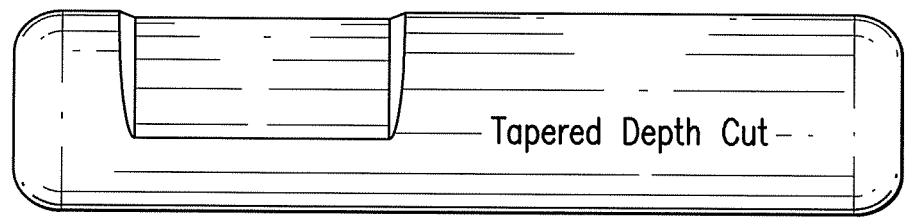
FIG. 12A is an illustration of a sensor core of an implantable sensor showing a saddle cut on the sensor core with a tapered depth cut in accordance with an embodiment of the present invention.
Figure 12B:
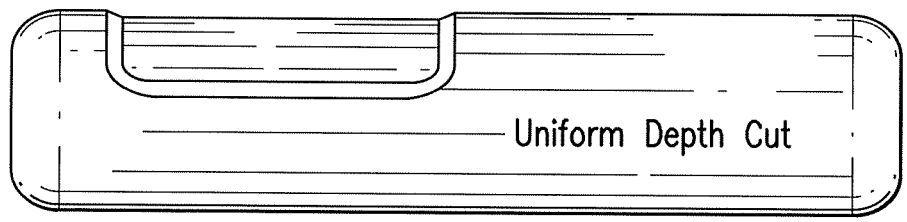
FIG. 12B is an illustration of a sensor core of an implantable sensor showing a saddle cut on the sensor core with a uniform depth cut in accordance with an embodiment of the present invention.
Figure 12C:
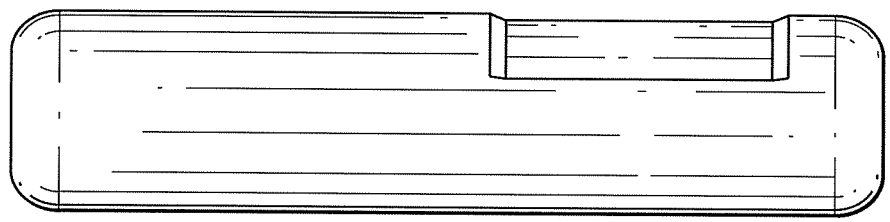
FIG. 12C is a design diagram of a saddle cut sensor core according to an embodiment of the invention.
Figure 12D:
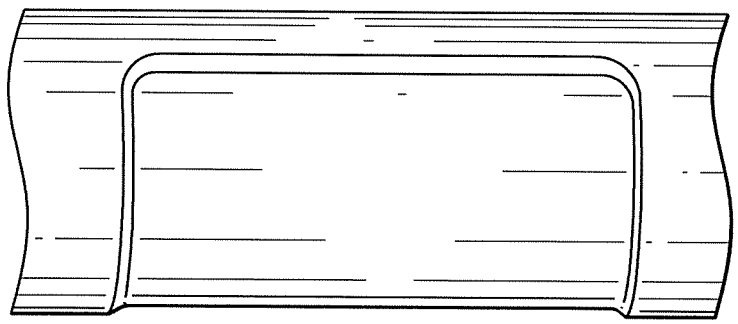
FIG. 12D is a top view illustration of a uniform depth saddle cut sensor core in accordance with an embodiment of the present invention.

FIGS. 11A and 11B illustrate a representative sensor device that may be used in the context of the present invention. In particular, FIGS. 11A and 11B show a polymer encasement 1103 containing microelectronics 1105 in the interior 1104 of a representative electro-optical sensing device. The microelectronics 1105 may comprise microelectronic components such as, for example, a radiation source 1102 and a detector 1101. In one preferred embodiment, radiation source 1102 is an LED, although other radiation sources may be used. Also in one preferred embodiment, detector 1101 is a photosensitive element (e.g. a photodetector, photodiode), although other detecting devices may be used. Microelectronics that may be contained in a representative electro-optical sensing device are described in U.S. Pat. No. 6,330,464, which is incorporated by reference herein in its entirety.

As shown in more detail in FIG. 11B, the surface of the sensor device comprises a tortuous membrane with a platinum metal coating 1004 covering a porous sensor graft 1000, as similarly seen in FIG. 10B.

Metals within the scope of the invention (e.g. platinum, palladium, etc.) used as sputter coatings do not cause concern for potential clogging or fouling of the pores of the sensor graft. For example, the atomic radius of a platinum atom is 135 pm, with a diameter of 270 pm, i.e. a platinum atom has a diameter of 0.27 nm. Thus, a sputter coating of platinum that is about 3 nm thick, on top of the sensor graft surface, would be about 11 platinum atoms thick. Similarly, an about 6 nm thick platinum coating would be about 22 platinum atoms thick. So, a narrowing of a 1 µm (1,000 nm) wide macro-pore by the thickness of a metal coating on the pore wall by 6 nm would leave a pore diameter of 994 nm, which is not a significant constriction of the pore. Similarly, with a gold sputter coating, the largest diameter of the macro-pores of the porous sensor graft as seen in the SEM image of FIG. 9 is about 1 µm.

Because the sputter coating process disclosed does not completely fill in the macro-pores of a porous sensor graft, but rather lines the exterior macro-pores, some embodiments of the invention can retain the advantages of an intentionally porous structure. Alternatively, non-porous structures can be sputter coated to achieve the same goal of preventing degradation by ROS. Sputter deposited catalytic coatings that have a relatively fast rate of oxidizer degradation may alternatively or also be applied adjacent to oxidation sensitive materials, such as the porous sensor graft in embodiments of the present invention, and effectively prevent oxidative degradation of those oxidation sensitive materials. For example, for a sensor (or other device) that has an oxidation sensitive region on only one half or less of the sensor, or on a part of its surface, a sputter coating can be applied to the opposite side (i.e. back side) of that sensor (similar to the structural encasement embodiment seen in FIG. 6H), and the proximity of the coating can be sufficient to protect the functional elements of the sensor from oxidation, due to the fast kinetic degradation rate of ROS. The sputtered coating does not have to be continuous; it can be applied as one or more regions of sufficient area, proximity, and/or shape as needed to provide the amount (in terms of area and/or mass) of catalyst to achieve the needed rate of oxidizer decomposition to protect the device, sensor, or material. Alternatively, the desired coating of sputtered material could be made by simply masking the sensor or device surface before putting it into the sputter chamber, allowing for the deposition of sputtered catalytic material according to the shape and placement of catalyst desired.

For testing purposes, sputter coating was conducted with a platinum target resulting in a platinum coating on a sensor core (a sensor body according to an embodiment of the invention without the internal power source, transmitter, etc.). In terms of weight, the total amount of platinum sputtered onto the porous sensor graft surface is expected to be approximately 10 µg. This determination is made from sensor core surface area estimation, metal density, and nominal metallization thickness (about 3 nm). The corresponding weight of palladium is approximately 5 µg for the same metallization thickness.

In order to efficiently sputter coat the porous sensor grafts, embodiments of the sensor cores were modified to have a "saddle cut" along part of the sensor core length. In some embodiments, this saddle cut is a recessed, uniform depth, pocket that is machined into the surface of the sensor body that allows for the co-polymerization fabrication of the indicator monomers with the porous sensor graft material to be cast in that pocket region of the sensor body. In embodiments, the porous sensor grafts with indicator macromolecules are located within these regions. The saddle cut localizes the area of porous sensor graft with indicator macromolecules, and thus the area for sputter coating, which helps to minimize any parasitic interference with inductive power telemetry from the sensor when functioning in vivo. Further, the saddle cut allows for efficient setup of the sensor in a sputter chamber, removing the need for rotation of the sensor core because only a localized area requires coating. In other embodiments of the invention, more than one side or region of the sensor core can be sputter coated. In yet further embodiments of the invention, the coating area can have suitable shapes, such as, for example, round, square, rectangular, or even a region that continually surrounds the sensor core, so long as the dimensions and geometry of the sputter coating accommodates the function of the sensor.

Figure 13:
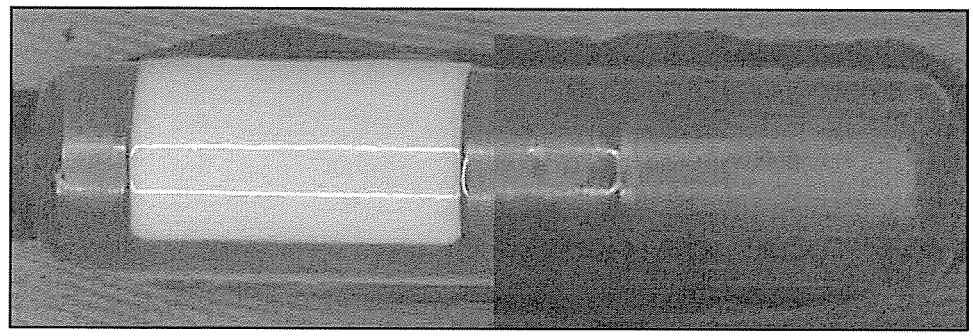
FIG. 13 is an image of a saddle cut sensor core with indicator macromolecule rehydrated on the surface.
Figure 14:
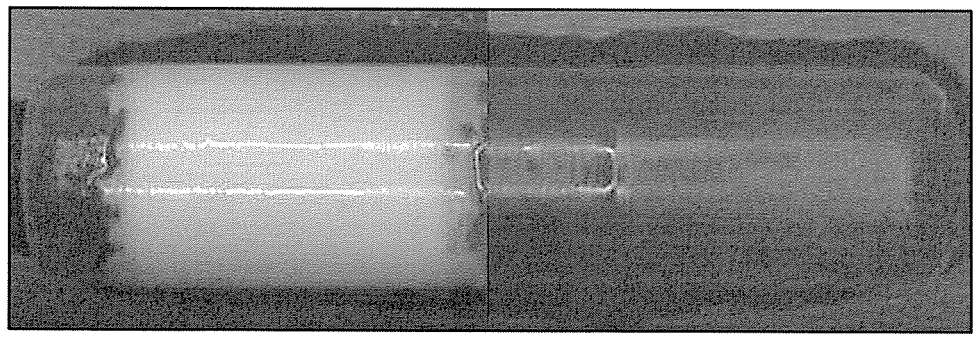
FIG. 14 is an image of a 360 degree cut sensor core with indicator macromolecule rehydrated on the surface.
Figure 15:
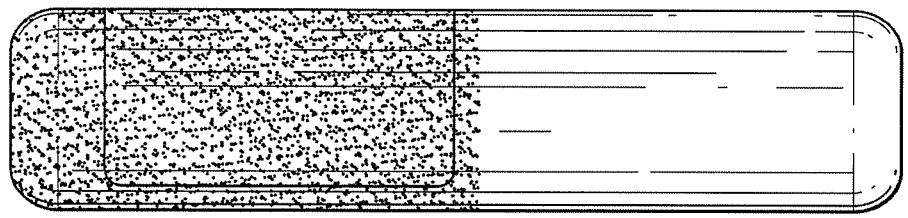
FIG. 15 is an illustration of where on a saddle cut sensor core a sputtered metal layer would be applied.

Embodiments of the inventions are further shown and illustrated in FIGS. 12-16. FIG. 12A illustrates a side profile image of the saddle cut with a tapered depth cut. 12B illustrates a side profile image of the saddle cut with a uniform depth cut. FIG. 12C is a design schematic for the saddle cut sensor core. FIG. 12D is an illustration of a top view of a uniform depth saddle cut sensor core. FIGS. 13 and 14 show the difference between a saddle cut sensor core (FIG. 13) and the standard "360 degree cut" sensor core (FIG. 14). The sensor core in FIGS. 13 and 14 have been submersed in buffer, and the region with rehydrated indicator macromolecules is seen as opaque and white. As seen in FIG. 14, a saddle cut graft is not required for all embodiments of the present invention; the porous sensor graft may be protected whether it is located in a specific region of a sensor body or completely covering a sensor body. FIG. 15 is a further illustration of where a saddle cut sensor core would be exposed to sputtering (as illustrated, the left half of a sensor core having a porous sensor graft region) in order to protect the region of porous sensor graft with indicator molecules.

Other configurations or cuts may be used if manufacturing considerations or in vivo functionality are enhanced by such configurations. For example, the sensor cores may be cut according to other geometries, have perforations of a various depths that can be sputtered, or be surrounded by a film (that can be applied to any shape of device) that has been sputtered separately from the sensor core.

Figure 16A:
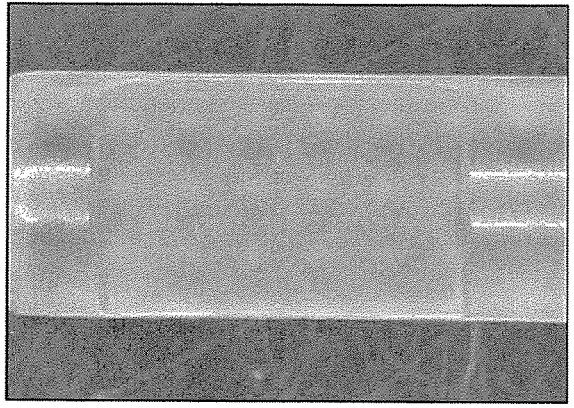
FIGS. 16A and 16B are images of a saddle cut sensor core with a platinum layer sputtered on top of it.
Figure 16B:
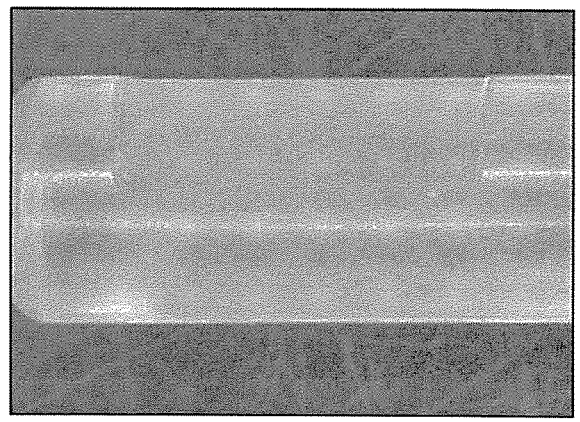
Figure 16C:
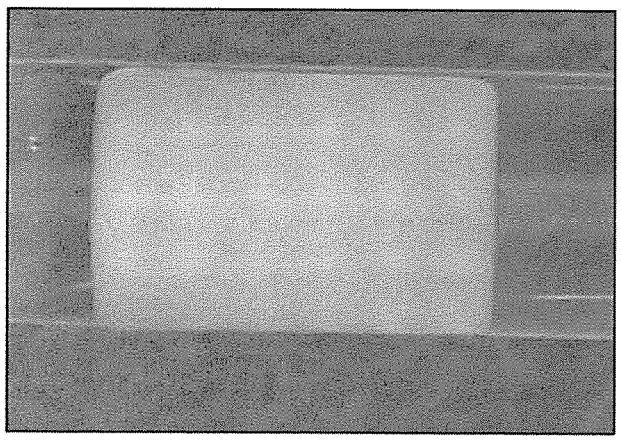
FIG. 16C is an image of a saddle cut sensor core with a platinum layer sputtered on top of it after the indicator macromolecules have been exposed to buffer and rehydrated.

FIGS. 16A and 16B are images that show a saddle cut core with dried, indicator layers (porous sensor graft) which has been sputtered with 3 nm of platinum, deposited with argon plasma. There is no visible evidence of the platinum coating because the layer is so thin. Upon submersion in buffer, the clear dried (sputtered) graft is rehydrated to the white opaque functional state as shown in FIG. 16C. No evidence of the surface metallization is visible because the metallization layer at 3 nm is only about 11 atoms thick.

Figure 17A:
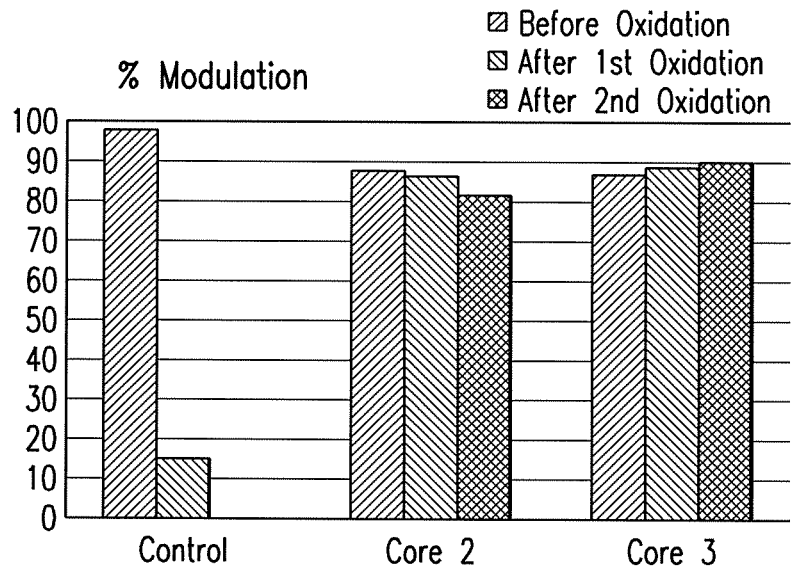
FIGS. 17A and 17B are graphical data relating to the modulation of light intensity from sensor cores, both with and without layers of sputter coated platinum, and the effect of the sputter coated platinum on exposure to hydrogen peroxide.
Figure 17B:
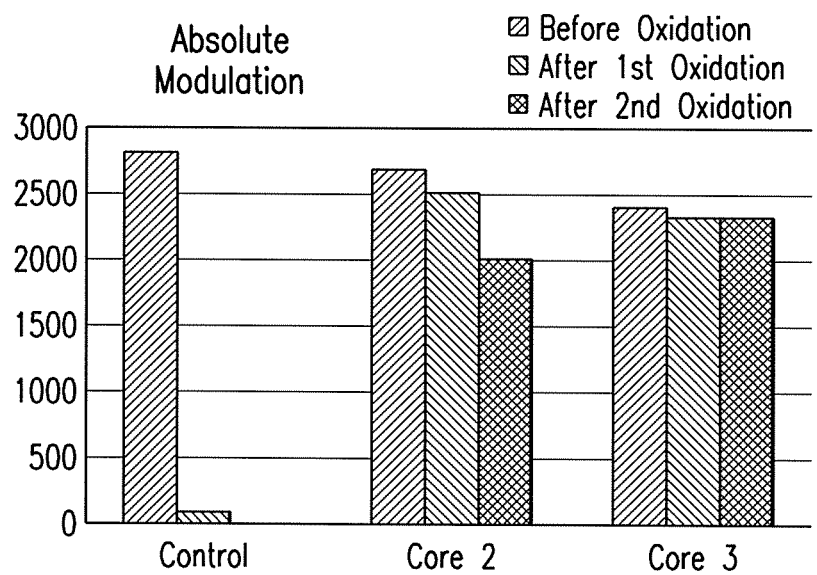

FIGS. 17A and 17B present modulation data of signal intensity from three sensor cores (in terms of percentage of modulation and absolute modulation, respectively). Modulation refers to the signal intensity measured from the sensor cores. Three saddle cut cores were tested, one control that did not undergo sputter coating, and "core 2" and "core 3" which were sputtered with platinum at two different thicknesses, where core 3 had a thicker platinum layer than core 2.

Before the hydrogen peroxide treatment, each core was measured with a fluorometer for signal intensity in the presence of 0 mM glucose and 18 mM glucose. Next, each core was submerged in 0.2 mM hydrogen peroxide in buffer at 37° C. for 24 hours then tested again for signal intensity. The signal intensity of the unprotected core was destroyed within only one 24 hour treatment with hydrogen peroxide. Core 2 and core 3 remained unaffected (within experimental error). The system was reloaded for core 2 and core 3 for a second 24 hour hydrogen peroxide exposure session. After the second oxidation, a total of 48 cumulative hours of hydrogen peroxide exposure, neither core 2 nor core 3 showed significant degradation due to hydrogen peroxide. The data for core 3 with a thicker platinum layer on the surface appears slightly better (more protected), although this may be experimental error in the spectrometer setup or the result of a very small sampling.

FIGS. 17A and 17B show that after 24 hours of submersion in 0.2 mM hydrogen peroxide, the control sample core which was not sputter coated with platinum had its signal destroyed by hydrogen peroxide exposure. In contrast, cores with platinum sputtered coatings were completely protected throughout the same period. This demonstrates the in vitro effectiveness of the very thin sputtered catalyst on the surface of the graft to protect the graft indicator layer from oxidation due to high ambient concentrations of hydrogen peroxide.

The purpose of this invention is to protect against major signal loss caused by oxidation both during wound healing as well as lower-level chronic oxidation during the lifetime of the sensor. If a device is protected from oxidation that occurs during wound healing, it becomes the lower-level chronic oxidation that ultimately establishes the useful life of a sensor implant. A protective layer preventing oxidation from long-term foreign body response will greatly extend the useful life of the sensor.

An additional important performance factor for in vivo devices is the extension of time between calibration. A device with a longer recalibration interval is better for a user, both in cost and in health due to the increased life of the sensor. Typically a sensor that is otherwise mechanically, chemically, and electrically stable will remain in calibration for as long as analyte concentration is the only variable. However, under chronic oxidation, a steady degradative change is imposed on the device by oxidation of indicator or materials of construction, thereby causing a mechanical and/or chemical change beyond that which is attributed only to analyte changes. For a sensor using a chemical or biochemical transduction system, progressive oxidation of indicator amounts to a second variable that is manifest as signal drift or decay over time. Any signal movement that is not caused by the analyte, or that is understood and compensated for by the signal processing system causes the sensor to drift out of calibration and must be re-calibrated to back within its performance standard. By eliminating, or even slowing down oxidation of indicator or any material component within the sensor transduction system, the recalibration interval is extended. Some in vivo sensors can require as many as three recalibrations per 24 hour period. A sensor that needs to be recalibrated for significantly longer intervals, such as only once per week, per month, or per quarter, would have much higher value to users. In embodiments of the invention, if the indicator molecules are sufficiently protected such that there is not a drastic loss of signal, or if degradative change is stopped entirely, then the only calibration needed will be at the time of manufacture.

A study was conducted to evaluate the protection of an implanted sensor from ROS degradation in humans by use of a plasma sputtered platinum porous catalytic diffusion barrier installed onto the surface of the sensor. In this study, twenty one sensors were sputtered with metallic platinum to a depth of 3 nanometers using an Electron Microscopy Sciences EMS150TS. The plasma chamber of the EMS150TS was flushed, evacuated, and backfilled with argon gas to 0.01 mbar. The current was set at 25 mA, and the platinum thickness was determined by a thickness monitor mounted within the chamber. After platinum deposition, sensors were packaged for sterilization by ethylene oxide and stored at 70% relative humidity (RH).

All twenty one experimental, platinum sputtered sensors were implanted into the subcutaneous space above the fascia in the dorsal wrist area for twelve human (type 1 diabetic) volunteers. Similarly, 12 control sensors without platinum treatment were implanted into the same wrist location for seven type 1 diabetic human volunteers. The subject identification numbers include either an "LA" or an "RA" to designate whether that sensor was implanted in the left arm or right arm, respectively. The data presented is the modulation taken from the sensor's wireless telemetry feed to an external reader.

Table 1 presents the comparative results from in vivo implants. The data from the control sensors was reported at days 7, 10, 16, 23, and 28 during implant. The data from the experimental, platinum sputtered sensors was reported at days 3, 13, 21, 26, and 29 after implant.

TABLE 1

| Subject | | Modulation remaining at each read session | | | | |
|---|---|---|---|---|---|---|
| Controls | Lot # | Day 7 | Day 10 | Day 16 | Day 23 | Day 28 |
| D05 LA | 03052011 | 33% | 32% | 31% | 19% | 18% |
| D05 RA | 03252011 | 0% | 0% | 0% | 0% | 0% |
| D06 LA | 03052011 | 66% | 56% | 55% | 53% | 52% |
| D06 RA | 03252011 | 0% | 0% | 0% | 0% | 0% |
| D07 LA | 03052011 | 59% | 58% | 57% | 50% | 48% |
| D07 RA | 03252011 | 72% | 71% | 34% | 23% | 22% |
| D08 LA | 03052011 | 86% | 85% | 37% | 33% | 30% |
| D08 RA | 03252011 | 22% | 22% | 21% | 20% | 20% |
| D09 LA | 03052011 | 53% | 52% | 51% | 49% | 48% |
| D09 RA | 03252011 | 0% | 0% | 0% | 0% | 0% |
| D10 RA | 03252011 | 47% | 46% | 45% | 41% | 40% |
| D11 LA | 03252011 | 0% | 0% | 0% | 0% | 0% |
| Combined | | 37% ± 32% | 35% ± 31% | 28% ± 23% | 24% ± 21% | 23% ± 20% |
| Platinum Sputtered | | Day 3 | Day 13 | Day 21 | Day 26 | Day 29 |
| D18 LA | 05202011 | 98% | 94% | 91% | 90% | 88% |
| D18 RA | 05202011 | 94% | 91% | 88% | 87% | 85% |
| D19 LA | 05202011 | 92% | 90% | 77% | 75% | 74% |
| D19 RA | 05202011 | 91% | 78% | 76% | 75% | 73% |
| D20 LA | 05202011 | 72% | 69% | 67% | 66% | 65% |
| D21 RA | 05202011 | 87% | 83% | 80% | 79% | 77% |
| D22 LA | 05202011 | 90% | 81% | 79% | 77% | 75% |
| D23 LA | 06032011 | 92% | 88% | 85% | 83% | 82% |
| D23 RA | 05202011 | 84% | 74% | 66% | 62% | 60% |
| D24 LA | 06032011 | 98% | 92% | 88% | 85% | 84% |
| D24 RA | 05202011 | 85% | 74% | 67% | 63% | 60% |
| D25 LA | 06032011 | 91% | 84% | 79% | 76% | 74% |
| D25 RA | 05202011 | 89% | 83% | 78% | 76% | 74% |
| D26 LA | 06032011 | 99% | 94% | 91% | 89% | 88% |
| D26 RA | 06032011 | 99% | 94% | 91% | 89% | 88% |
| D27 LA | 07222011 | 99% | 94% | 91% | 89% | 88% |
| D27 RA | 07222011 | 94% | 90% | 87% | 85% | 84% |
| D28 LA | 07222011 | 75% | 71% | 67% | 65% | 64% |
| D28 RA | 07222011 | 95% | 91% | 88% | 86% | 85% |
| D29 LA | 07222011 | 99% | 95% | 91% | 90% | 88% |
| D29 RA | 07222011 | 95% | 90% | 86% | 84% | 83% |
| Combined | | 91% ± 7.5% | 86% ± 8.3% | 82% ± 8.9% | 80% ± 9.3% | 78% ± 9.5% |

As can be seen from the data in Table 1, the platinum surface diffusion barrier preserves signal relative to the untreated devices by a factor of more than double. Importantly, no sensors using the platinum sputter treatment are degraded to zero as is typical in the untreated group. The data shows that platinum is providing local protection of the indicator system within the microenvironment of the indicator graft without interfering with normal heal-up reactions requiring ROS that may be ongoing in the surroundings. Further, the significant sensor-to-sensor and/or subject-to-subject variability in modulation remaining displayed in the control group is not seen in the experimental, platinum sputtered group.

Table 2 presents expected life time data for the in vivo implants in Table 1. The expected life time of the implant is calculated by a curve fit extrapolation. In Table 2, the columns give data in terms of a range of days and a number of visits. The data collected from within specified range of days was used to calculate and extrapolate the expected useful life of the sensor before its signal would drop too low to maintain accuracy specification. After implant of a device or material, the natural heal-up process continues which includes ROS of the inflammation response. Thus, a calculation made at a later time interval within or after the heal-up period might be expected to be more representative of the full lifetime of the implanted device or material than one made close after implant when healing is just getting started. Data used toward the end of the period would be expected to be more settled and more accurate than data from earlier because the heal-up process is more settled toward the end of the period. The visits noted in each column refer to the number of visits into the clinic the patient has made post-implant by the time the measurements used in the calculation from the patient's implant are taken.

TABLE 2

| Subject | | Expected life time (days) | | | | | |
|---|---|---|---|---|---|---|---|
| Controls | Lot # | Day 7-10 (2 visits) | Day 7-16 (3 visits) | Day 7-23 (4 visits) | Day 7-28 (5 visits) | Day 10-28 (4 visits) | Day 16-28 (3 visits) |
| D05 LA | 03052011 | 335 | 335 | 77 | 79 | 73 | 65 |
| D05 RA | 03252011 | 0 | 0 | 0 | 0 | 0 | 0 |
| D06 LA | 03052011 | 63 | 146 | 215 | 253 | 377 | 398 |
| D06 RA | 03252011 | 0 | 0 | 0 | 0 | 0 | 0 |
| D07 LA | 03052011 | 370 | 389 | 225 | 228 | 214 | 190 |

TABLE 2-continued

| | | | | | | | |
|---|---|---|---|---|---|---|---|
| D07 RA | 03252011 | 395 | 45 | 45 | 54 | 55 | 88 |
| D08 LA | 03052011 | 403 | 43 | 54 | 66 | 70 | 123 |
| D08 RA | 03252011 | 218 | 234 | 238 | 239 | 241 | 242 |
| D09 LA | 03052011 | 320 | 368 | 374 | 377 | 383 | 382 |
| D09 RA | 03252011 | 0 | 0 | 0 | 0 | 0 | 0 |
| D10 RA | 03252011 | 359 | 360 | 242 | 243 | 222 | 211 |
| D11 LA | 03252011 | 0 | 0 | 0 | 0 | 0 | 0 |
| Combined | | 205 ± 177 | 160 ± 166 | 123 ± 129 | 128 ± 132 | 136 ± 145 | 142 ± 145 |

| Platinum Sputtered | | Day 3-13 (2 visits) | Day 3-21 (3 visits) | Day 3-25 (4 visits) | Day 3-29 (5 visits) | Day 13-29 (4 visits) | Day 21-29 (3 visits) |
|---|---|---|---|---|---|---|---|
| D18 LA | 05202011 | 418 | 419 | 420 | 420 | 421 | 422 |
| D18 RA | 05202011 | 405 | 407 | 408 | 409 | 411 | 412 |
| D19 LA | 05202011 | 443 | 250 | 252 | 264 | 239 | 431 |
| D19 RA | 05202011 | 151 | 214 | 244 | 272 | 424 | 431 |
| D20 LA | 05202011 | 403 | 403 | 403 | 403 | 403 | 403 |
| D21 RA | 05202011 | 398 | 413 | 417 | 420 | 430 | 430 |
| D22 LA | 05202011 | 268 | 328 | 352 | 357 | 422 | 379 |
| D23 LA | 06032011 | 439 | 438 | 438 | 435 | 433 | 431 |
| D23 RA | 05202011 | 126 | 142 | 184 | 211 | 246 | 319 |
| D24 LA | 06032011 | 205 | 346 | 371 | 395 | 469 | 470 |
| D24 RA | 05202011 | 81 | 188 | 176 | 191 | 232 | 188 |
| D25 LA | 06032011 | 107 | 198 | 262 | 307 | 428 | 440 |
| D25 RA | 05202011 | 123 | 218 | 282 | 324 | 431 | 441 |
| D26 LA | 06032011 | 467 | 469 | 470 | 470 | 470 | 468 |
| D26 RA | 06032011 | 453 | 454 | 455 | 453 | 453 | 451 |
| D27 LA | 07222011 | 463 | 461 | 461 | 461 | 460 | 460 |
| D27 RA | 07222011 | 511 | 513 | 514 | 513 | 513 | 512 |
| D28 LA | 07222011 | 182 | 294 | 353 | 353 | 442 | 451 |
| D28 RA | 07222011 | 469 | 476 | 479 | 475 | 475 | 471 |
| D29 LA | 07222011 | 449 | 447 | 449 | 450 | 450 | 451 |
| D29 RA | 07222011 | 248 | 348 | 394 | 420 | 466 | 469 |
| Combined | | 324 ± 149 | 354 ± 113 | 371 ± 100 | 381 ± 89 | 415 ± 78 | 425 ± 67 |

As can be seen from the calculated data in Table 2, the expected lifetime of an implant, as determined from the modulation of the sensor, greatly increases when the implant is protected with a platinum barrier layer sputtered onto its surface.

In other aspects, the present invention has application to any biomaterial or implanted material or device, where such materials or devices may be passive, structural, or functional in nature, that may be susceptible in some way to in vivo inflammation reaction. Exemplary, non-limiting, applications of this invention are set forth below.

Continuous glucose monitors other than the embodiments disclosed above in this application would also likely benefit from this invention. For example, transcutaneous needle-type indwelling continuous glucose monitor (CGM) devices also interface directly with subcutaneous tissue in such a way as to stimulate local inflammation and foreign body response. The body would respond to these intrusions of foreign material and mechanical tissue insult just as a completely implantable device. It is expected that hydrogen peroxide and ROS would have the same effect in causing substantial oxidative damage to any chemically or biochemically transduced system and thus benefit from the invention.

In particular, glucose oxidase sensors that use hydrogen peroxide as a part of their sensing functionality often need to prevent hydrogen peroxide from freely entering an in vivo environment. Such sensors may use additional catalyses to degrade hydrogen peroxide or use a laminate as a part of the sensor to prevent hydrogen peroxide from entering and/or aggregating in an in vivo environment. The catalytic protection disclosed in this application may be applied to such devices.

All implants, whether they are active (such as a sensor) or passive materials (such as in orthopedic or cosmetic applications), are exposed to living tissue and fluids and are thus susceptible to oxidation via the body's normal response system. Living cells produce reactive oxygen species such as hydrogen peroxide in what is commonly known as localized inflammation and foreign body response stimulated either directly by the material/device implanted, and/or by the inevitable tissue disruption repair caused by physically implanting the material or device. Typically devices or materials are compromised by oxidative assault in living tissue. Such devices can include, without limitation, pacemakers, joint implants, bandages, orthopedic devices, cosmetic or reconstructive surgery implants, or time release porous polymer material implants for leaching drug delivery. Exemplary implanted biomaterials can include materials such as polyurethane and other polymers. The compromise may be manifest as structural weakening, degradation in properties, loss of functionality, or alteration in the chemical structure itself to a different composition than intended. These oxidation assaults are normal, but often either shorten the useful life, compromise optimal performance, or cause the outright failure of the implant. According to the present invention, the application of very thin, in some embodiments submicron, layers of a protective barrier from about 0.5 nm to about 2.5 mm in thickness applied to implanted materials of exposure can protect the device locally from oxidation by ROS.

Figure 18:
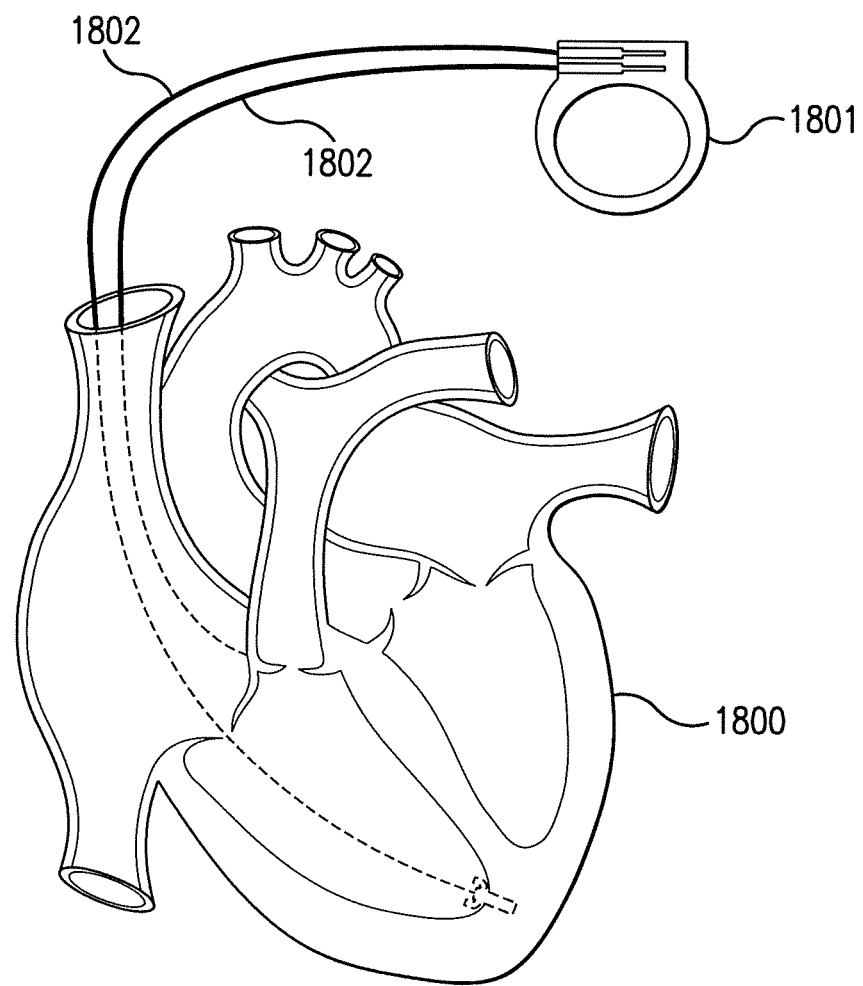
FIG. 18 is an illustration of a pacemaker that can be incorporated with a protective material according to an embodiment of the present invention.

In an alternative embodiment of the invention, as seen in FIG. 18, a catalytic barrier that prevents ROS driven oxidation may be applied to a pacemaker, comprising at least an electrical generator 1801 of the pacemaker and pacemaker leads 1802 implanted to regulate a heart 1800. A pacemaker is subject to inflammation response and to chronic foreign-body response and the associated ROS driven oxidation. In particular, a catalytic barrier can be applied to pacemaker leads 1802 in the form of a structural encasement at least partially encasing the pacemaker leads 1802, or a coating applied to the pacemaker leads 1802 potentially through sputter deposition, in accordance with embodiments of the present invention.

Alternatively, an inflammation reaction can occur on the external surface of skin in response to stimuli including, without limitation, polymer adhesives in EEG or EKG patches, watch bands, earrings, or any other material to which a human has an acute sensitivity or allergy. According to the present invention, the application of very thin, in some embodiments submicron, layers of a protective barrier from about 0.5 nm to about 2.5 mm in thickness applied to such materials can protect such materials from ROS.

Any other exposure within other non-implant environments or applications where exposure to hydrogen peroxide (ROS) may compromise, or degrade the performance of a material or molecule, or device functionality, would also benefit from this invention. Molecules, microcircuit, optical, chemical, or micromechanical constructs may be encased within porous protective layers, metalized from the outside, and allow free diffusion access to the intended molecules but provide a protective barrier against damaging peroxides and other ROS which are degraded to harmless oxygen and water at the layer of metallization. Devices benefiting from protection but not requiring diffusive access to analytes, such as devices with RFID components, can benefit by direct metallization onto the surface of the material without a porous coating. Further, applications that do not apply a metal film to a porous surface may have a thickness that is appropriate to adequately protect a more uniform surface.

While the invention has been described in detail above, the invention is not intended to be limited to the specific embodiments as described. It is evident that those skilled in the art may now make numerous uses and modifications of and departures from the specific embodiments described herein without departing from the inventive concepts.

The invention claimed is:

1. A system comprising:
   (a) a device configured for implantation or insertion into the body of an animal; and
   (b) a protective material in close proximity to a surface of the device, wherein:
      (1) the protective material prevents or reduces degradation or interference of the device due to inflammation reactions and/or foreign body response;
      (2) the protective material comprises a metal or metal oxide which catalytically decomposes or inactivates in vivo reactive oxygen species or biological oxidizers; and
      (3) the thickness of the protective material is in a range from about 1 nm to about 20 nm.

2. The system of claim 1, wherein the device is a sensor.

3. The system of claim 2, wherein the sensor is for monitoring glucose levels.

4. The system of claim 2, wherein the sensor comprises a body at least partially surrounding a photosensitive detector element and a light source, and further wherein an external surface of the sensor body comprises a porous sensor graft layer that comprises one or more indicator macromolecules.

5. The system of claim 4, wherein the one or more indicator macromolecules comprises a phenylboronic acid residue.

6. The system of claim 1, wherein the metal or metal oxide comprises silver, palladium, platinum, manganese, or alloys, or gold-inclusive alloys, or combinations thereof.

7. The system of claim 1, wherein the device is a material that is sensitive to, or is susceptible to damage from, oxidation.

8. The system of claim 1, wherein the protective structure is in close proximity to at least a part of the device that comprises a polymer.

9. The system of claim 1, wherein the thickness of the protective material is in a range from about 3 nm to about 6 nm.

10. A system comprising:
    (a) a device configured for implantation or insertion into the body of an animal; and
    (b) a layer of protective coating applied onto the device wherein:
       (1) the protective coating prevents or reduces degradation or interference of the device from inflammation reactions and/or foreign body response;
       (2) the protective coating comprises a metal or metal oxide which catalytically decomposes or inactivates in vivo reactive oxygen species or biological oxidizers; and
       (3) the thickness of the protective coating is in a range from about 1 nm to about 20 nm.

11. The system of claim 10, wherein the device is a sensor.

12. The system of claim 11, wherein the sensor is for monitoring glucose levels.

13. The system of claim 11, wherein the sensor comprises a body surrounding a photosensitive detector element and a light source, and further wherein an external surface of the sensor body comprises a porous sensor graft layer that comprises one or more indicator macromolecules.

14. The system of claim 13, wherein the one or more indicator macromolecules comprises a phenylboronic acid residue.

15. The system of claim 13, wherein the sensor body has a saddle-cut shape.

16. The system of claim 10, wherein the protective coating is applied by sputter deposition.

17. The system of claim 10, wherein the metal or metal oxide comprises silver, palladium, platinum, manganese, or alloys, or gold-inclusive alloys, or combinations thereof.

18. The system of claim 10, wherein the thickness of the protective coating is in a range from about 3 nm to about 6 nm.

19. The system of claim 10, wherein the thickness of the protective coating is about 1 nm thick.

20. The system of claim 10, wherein the device is a material that is sensitive to, or is susceptible to damage from, oxidation.

21. The system of claim 10, wherein the protective coating is applied onto at least a part of the device that comprises a polymer.

22. The system of claim 10, wherein the device has an in vivo functionality for a substantially elongated period of time, as compared to the useful life of a separate material with in vivo utility but without the layer of protective coating, following implant in an environment where the implantable device is exposed to inflammation reactions and/or foreign body response.

23. A glucose sensor for determining the presence or concentration of glucose in an animal, said sensor comprising:
    (a) a sensor body having an outer surface surrounding said sensor body;
    (b) a radiation source in said sensor body which emits radiation within said sensor body;
    (c) an indicator element that is affected by the presence or concentration of glucose in said animal, said indicator element being positioned in close proximity to at least a portion of said outer surface of said sensor body;

(d) a photosensitive element located in said sensor body and positioned to receive radiation within the sensor body, said photosensitive element configured to emit a signal responsive to radiation received from said indicator element and which is indicative of the presence or concentration of glucose in said animal; and (e) a protective coating comprising silver, palladium, platinum, manganese, or alloys, or gold-inclusive alloys, or combinations thereof, at least partially covering said indicator element, wherein the thickness of the protective barrier is in a range from about 1 nm to about 20 nm.

24. The sensor of claim 23, wherein the outer surface is comprised of a polymer.

25. The sensor of claim 23, wherein the indicator element comprises at least one indicator macromolecule.

26. The sensor of claim 23, wherein the protective coating is further comprised of oxides of silver, platinum, palladium, manganese, alloys, or gold-inclusive alloys, or combinations thereof.

* * * * *